(12) United States Patent
Rodriguez Sarmiento et al.

(10) Patent No.: US 8,598,357 B2
(45) Date of Patent: Dec. 3, 2013

(54) BENZODIOXOLE PIPERIDINE COMPOUNDS

(75) Inventors: Rosa Maria Rodriguez Sarmiento, Basel (CH); Juergen Wichmann, Steinen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 135 days.

(21) Appl. No.: 13/405,392

(22) Filed: Feb. 27, 2012

(65) Prior Publication Data

US 2012/0225868 A1 Sep. 6, 2012

(30) Foreign Application Priority Data

Mar. 3, 2011 (EP) ..................................... 11156787

(51) Int. Cl.
*C07D 211/22* (2006.01)
*A61K 31/445* (2006.01)

(52) U.S. Cl.
USPC .......................................... 546/197; 514/321

(58) Field of Classification Search
USPC .......................................... 514/321; 546/197
See application file for complete search history.

(56) References Cited

FOREIGN PATENT DOCUMENTS

| WO | 96/39133 | 12/1996 |
| WO | 2009/013212 | 1/2009 |
| WO | 2010/031735 | 3/2010 |

OTHER PUBLICATIONS

"International Search Report PCT/EP2012/053387 mailed Apr. 11, 2012".
Lieberman et al., "N. Engl. J. Med." 353:1209-1223 ( 2005).
Howard et al., "Annual Reports in Medicinal Chemistry" 28:39 ( 1993).
Moore et al., "European Journal of Pharmacology" 237:1-7 ( 1993).
Ashby et al., "Synapse" 48:154-156 ( 2003).
Campos et al., "Soc. Neurosci. Online Abstract 322.8" ( 2003).
Harrison et al., "British Journal of Psychiatry" 174( Suppl 38):12-22 ( 1999).
Deangelis et al., "Curr. Opin. Investig. Drugs" 3:106-112 ( 2002).
"International Search Report PCT/EP2012/052440 mailed Apr. 11, 2012".
Levitan et al., "Journal of Affective Disorders" 71:229-233 ( 2002).
Reavill et al., "J. Pharmacol. Exp. Ther." 294:1154-1165 ( 2000).
Gackenheimer et al., "Journal of Pharmacology & Experimental Therapeutics" ;274:1558-1565 ( 1995).
Drescher et al., "Am. Soc. Neurosci." 894:6 ( 2002).
Porras et al., Neuropsychopharmacology 26:311-324 ( 2002).
Leikin et al., Med. Toxicol. Adverse Drug Exp. 4:324-350 ( 1989).
Joyce et al., "Drug Discovery Today 1" 10(13):917-925 ( 2005).
Spurlock et al., Mol. Psychiatry 3:42-49 ( 1998).
Arranz et al., Lancet 355:1615-1616 ( 2000).
Roth et al., "Nat. Rev. Drug Discov." 3:353-359 ( 2004).
Wiecki et al., "Psychopharmacology" 204:265-277 ( 2009).
Vorel et al., "J. Neurosci." 22:9595-9603 ( 2002).
Belliotti, T. R., "Bioorganic & Medicinal Chemistry Lett." 7:2403 ( 1997).
Retz et al., "J. Neural. Transm." 110:531-572 ( 2003).
Gurevich et al., "Archives of General Psychiatry" 54:225-232 ( 1997).
Millan et al., "The Journal of Pharmacology & Experimental Therapeutics" 324:1212-1226 ( 2008).

*Primary Examiner* — John Mabry

(57) ABSTRACT

The present invention is concerned with novel dual modulators of the 5-$HT_{2A}$ and $D_3$ receptors of formula (I)

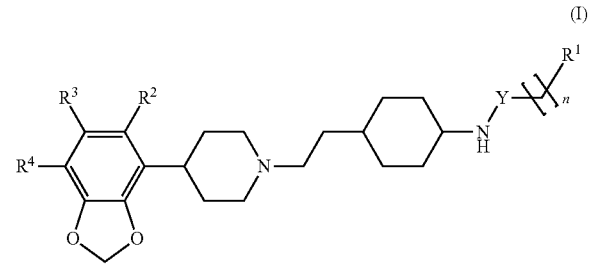

(I)

wherein n, Y, $R^1$, $R^2$, $R^3$, and $R^4$ are as described herein, as well as pharmaceutically acceptable salts and esters thereof. Further the present invention is concerned with the manufacture of the compounds of formula (I), pharmaceutical compositions containing them and their use as pharmaceuticals.

25 Claims, No Drawings

BENZODIOXOLE PIPERIDINE COMPOUNDS

PRIORITY TO RELATED APPLICATION(S)

This application claims the benefit of European Patent Application No. 11156787.1, filed Mar. 3, 2011, which is hereby incorporated by reference in its entirety.

BACKGROUND OF THE INVENTION

Dopamine, a major catecholamine neurotransmitter, is involved in the regulation of a variety of functions which include emotion, cognition, motor functions, and positive reinforcement. The biological activities of dopamine are mediated through G protein-coupled receptors (GPCRs) and in human, five different dopamine receptors $D_1$-$D_5$ have been identified, where the $D_2$-like receptors ($D_2$, $D_3$ and $D_4$) couple to the G-protein $G_{\alpha I}$. The $D_3$ dopamine receptor is most highly expressed in the nucleus accumbens and is proposed to modulate the mesolimbic pathway consisting of neuronal projections from the ventral tegmental area, hippocampus and amygdala to the nucleus accumbens, which projects to the prefrontal and cingulate cortices as well as various thalamic nuclei. The limbic circuit is thought to be important for emotional behavior and thus $D_3$ receptor antagonists are proposed to modulate psychotic symptoms such as hallucinations, delusions and thought disorder (Joyce J. N., Millan M. J., *Drug Discovery Today* (2005) 10:917-925). In addition, it has been reported that drug naive schizophrenic patients show altered levels of $D_3$ receptor expression (Gurevich E. V. et al., *Arch. Gen. Psychiatry* (1997) 54, 225-232) and dopamine release (Laruelle M., *Presentation at Institut de Recherches Internationales Servier Workshop on Schizophrenia: Pathological Bases and Mechanisms of Antipsychotic Action*, Chicago, Ill., 2000), indicating that a disturbed homeostasis of dopamine plays an important role in the etiology of schizophrenic symptoms.

The neurotransmitter serotonin (5-Hydroxytryptamine; 5-HT) is implicated in several psychiatric conditions including schizophrenia (Kandel E. R. et al. (eds.), *Principles of Neural Science* (2000) $3^{rd}$ edition, Appleton & Lange, Norwalk, Conn.). The involvement of serotonin in psychotic disorders is suggested by multiple studies which include treatment in humans with the psychotropic drug Lysergic acid (LSD; a serotonin agonist) which can induce schizophrenia-like symptoms such as hallucinations (Leikin J. B. et al., *Med. Toxicol. Adverse Drug Exp*. (1989) 4:324-350). Furthermore, altered brain distribution of serotonin receptors as well as an altered serotonergic tone, have been detected in schizophrenic patients (Harrison P. J., *Br. J. Psychiatry Suppl.* (1999) 38:12-22).

In mammals, serotonin exerts its biological activities through a family of 14 5-HT GPCRs. The $5$-$HT_{2A}$ receptor is most prominently expressed in the prefrontal cortex and at lower levels in the basal ganglia and the hippocampus in human brain, and is coupled predominantly to the G-protein Gαq. Genetic linkage studies of a $5$-$HT_{2A}$ polymorph to schizophrenia (Spurlock G. et al., *Mol. Psychiatry*. (1998) 3:42-49), as well as responsiveness to antipsychotic drugs (Arranz, M. J. et al., *Lancet* (2000) 355:1615-1616), further suggest a role for the $5$-$HT_{2A}$ receptor both in the treatment and pathology of psychosis. In addition, dopaminergic neurotransmission appears to be under the afferent regulation of the $5$-$HT_{2A}$ receptor (Porras G. et al., *Neuropsychopharmacology* (2002) 26:311-324). Overall $5$-$HT_{2A}$ receptor antagonists are proposed to be suitable for the treatment of disorders associated with dysfunctional dopaminergic systems. Moreover, $5$-$HT_{2A}$ receptor antagonism has been recognized as beneficial for the treatment of psychosis (de Angelis L., *Curr. Opin. Investig. Drugs* (2002) 3:106-112).

The $D_3$ and $5$-$HT_{2A}$ receptors besides the mentioned psychotic disorders are further reported to be linked to other psychoses including paranoia and delusions (Reavill C. et al., *JPET* (2000) 294:1154-1165; Harrison P. J., *Br. J. Psychiatry Suppl.* (1999) 38:12-22), to drug dependency, abuse and withdrawal (Vorel S. R. et al., *J. Neurosci.* (2002) 22:9595-9603; Campos A. C. et al., *Soc. Neurosci. Abstr.*, (2003) 322:8; Ashby C. R. et al., *Synapse* (2003) 48:154-156), attention deficit hyperactivity disorders (ADHD) (Retz W. et al., *J. Neural. Transm.* (2003) 110:531-572; Levitan R. D. et al., *J. Affective Disorder* (2002) 71:229-233), as well as to anxiety and depression (Reavill C. et al., *JPET* (2000) 294:1154-1165; Drescher K. et al. *Am. Soc. Neurosci.* (2002) 894:6).

Currently used medications to treat schizophrenia, bipolar mania and other psychoses, include both typical ($D_2$/$D_3$ preferring) or the more recent atypicals, which exhibit polypharma-cology interacting at multiple receptors (e.g., $D_1$, $D_2$, $D_3$, $D_4$, $5$-$HT_{1A}$, $5$-$HT_{2A}$, $5$-$HT_{2C}$, $H_1$, $M_1$, $M_2$, $M_4$, etc.)(Roth B. L. et al., *Nat. Rev. Drug Discov.* (2004) 3:353-359). These antipsychotics, although relatively successful (some patients exhibit treatment resistance) at treating the positive symptoms of schizophrenia, are less effective at treating negative symptoms, cognitive deficits, and associated depression and anxiety, all of which lead to reduced patient quality of life and socioeconomic problems. Furthermore, patient compliance is compromised by prevalent side effects such as weight gain, extrapyramidal symptoms (EPS), and cardiovascular effects (Lieberman J. A. et al., *N. Engl. J. Med.* (2005) 353:1209-1223).

Antipsychotic drug treatment has frequently been complicated by serious side effects of widespread $D_2$ antagonism, notably an extrapyramidal or parkinsonian syndrome caused by antagonism of the dopaminergic projection from substantia nigra to corpus striatum. $D_2$ receptor blockade induces catalepsy and has been associated with negative effects against cognition. Also preferential blockade of $D_3$ vs. $D_2$ receptors, preserves and/or enhances cognitive function, and increases frontocortical cholinergic transmission. (Joyce J. N., Millan M. J., *Drug Discovery Today* (2005) 10:917-925, Moore N. A. et al., *European Journal of Pharmacology* (1993) 237:1-7; Barth V. N., *Typical and atypical antipsychotics: Relationships between rat in vivo dopamine D(2) receptor occupancy assessed using LC/MS and changes in neurochemistry and catalepsy*. Dissertation Indiana University (2006); Millan M. J. et al., *Fr. Journal of Pharmacology and Experimental Therapeutics* (2008) 324:1212-1226; Wiecki T. V. et al., *Psychopharmacology* (2009) 204:265-277).

The typical antipsychotic agents on the market today display $D_2$ antagonism, and most have extrapyramidal side effects (EPS) such as pseudoparkinsonism and tardive dyskinesia (Howard H. R., Seeger T. F., *Annual Reports in Medicinal Chemistry* (1993) 28:39). It has been shown by selective binding experiments that $D_2$ receptors are more concentrated in the striatal regions of the brain, which are responsible for locomotor control than in the limbic regions which are responsible for thought processes. $D_3$ receptors are more concentrated in the limbic than in the striatal regions. It is therefore believed that selective $D_3$ ligands may relieve symptoms of schizophrenia without causing the EPS associated with blockade of $D_2$ receptors (Gackenheimer S. L. et al., *J. Phar-* macol. Exp. Ther. (1995) 274:1558, Belliotti T. R., Bioorg. Med. Chem. Lett. (1997) 7:2403).

SUMMARY OF THE INVENTION

The present invention provides dual modulators of the 5-HT$_{2A}$ and D$_3$ receptors, their manufacture, pharmaceutical compositions comprising them and their use as pharmaceuticals.

In particular, the present invention provides compounds of formula (I)

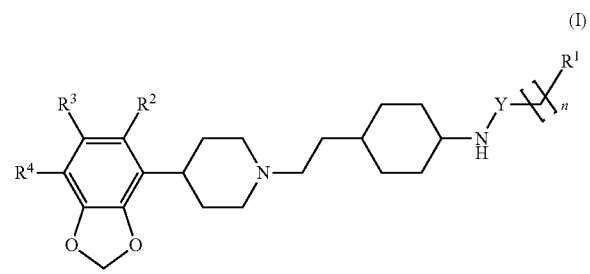

(I)

wherein R$^1$, R$^2$, R$^3$, R$^4$, n and Y are as described herein, and pharmaceutically acceptable salts and esters thereof.

The compounds of the invention are dual modulators of the 5-HT$_{2A}$ and D$_3$ receptors and are selective at the D$_2$ receptor. The compounds of the invention and their pharmaceutically acceptable salts have high affinity and selectivity for both, the dopamine D$_3$ and serotonin 5-HT$_{2A}$ receptors and are effective, alone or in combination with other drugs, in the treatment or prevention of psychotic disorders, as well as other diseases such as depression, anxiety, drug addiction, attention deficit hyperactivity disorders, dementia and memory impairment, while exhibiting fewer associated side effects. Psychotic disorders encompass a variety of diseases, which include schizophrenia, positive, negative and/or cognitive symptoms associated with schizophrenia, schizoaffective disorders, bipolar disease, mania, psychotic depression, and other psychoses involving paranoia and delusions.

In particular schizophrenia is characterized by complex symptomatology including positive symptoms, (i.e. delusions and hallucinations), and negative symptoms, (i.e. anhedonia, restricted fluency and productivity of thought and speech). In addition it is now well recognized that cognitive impairment is the third major diagnostic category of schizophrenia, characterized by loss in working memory as well as other deficits. Other symptoms include aggressiveness, depression and anxiety (Stahl, S. M., *Essential Psychopharmacology. Neuroscientific Basis and Practical Applications* (2000) 2$^{nd}$ edition, Cambridge University Press, Cambridge, UK).

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein may be appended to form chemically-relevant combinations, such as e.g. "heterocycloalkyl-aryl", "haloalkyl-heteroaryl", "arylalkyl-heterocycloalkyl", or "alkoxy-alkyl". The last member of the combination is a radical which is substituted by the other members of the combination in inverse order.

The term "substituent" denotes an atom or a group of atoms replacing a hydrogen atom on the parent molecule.

The term "compound(s) of this invention" and "compound(s) of the present invention" refers to compounds of formula (I) and stereoisomers, tautomers, solvates, and salts (e.g., pharmaceutically acceptable salts) thereof.

It will be appreciated, that the compounds of present invention can be derivatized at functional groups to provide derivatives which are capable of conversion back to the parent compound in vivo. Physiologically acceptable and metabolically labile derivatives, which are capable of producing the parent compounds of present invention in vivo are also within the scope of this invention.

The term "pharmaceutically acceptable esters" denotes derivatives of the compounds of present invention, in which a carboxy group has been converted to an ester, wherein carboxy group means —C(O)O—. Methyl-, ethyl-, methoxymethyl-, methylthiomethyl-, and pivaloyloxymethylesters are examples of such suitable esters. The term "pharmaceutically acceptable esters" furthermore embraces derivatives of the compounds of present invention in which hydroxy groups have been converted to the corresponding esters with inorganic or organic acids such as nitric acid, sulfuric acid, phosphoric acid, citric acid, formic acid, maleic acid, acetic acid, succinic acid, tartaric acid, methanesulfonic acid, or p-toluenesulfonic acid, and which are non toxic to living organisms.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid. The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. *Angew. Chem. Inter. Edit.* 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "stereoisomer" denotes a compound that possesses identical molecular connectivity and bond multiplicity, but which differs in the arrangement of its atoms in space.

The term "racemate" or "racemic mixture" refers to an equimolar mixture of two enantiomeric species, devoid of optical activity.

The term "trans-configuration" denotes the configuration within a molecule, wherein a pair of substituents is attached on opposite sides of a stereoisomeric group.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriat point. Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M Wuts, "*Protective Groups in Organic Synthesis*", 2nd ed., John Wiley & Sons, Inc., New York, N.Y., 1991, chapter 7; E. Haslam, "*Protective Groups in Organic Chemistry*", J. G. W. McOmie, Ed., Plenum Press, New York, N.Y., 1973, Chapter 5, and T. W. Greene, "*Protective Groups in Organic Synthesis*", John Wiley and Sons, New York, N.Y., 1981. The term "protected amino group" refers to an amino group substituted by an amino-protecting groups.

The term "deprotection" or "deprotecting" denotes the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "halo", "halogen", and "halide" are used interchangeably herein and denote fluoro, chloro, bromo, or iodo. Particular halo are fluoro and chloro.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, and tert-butyl. Particular alkyl are methyl, ethyl, isopropyl, iso-butyl and sec-butyl.

The term "alkoxy" denotes a group of the formula —O—R', wherein R' is an alkyl group. Examples of alkoxy moieties include methoxy, ethoxy, isopropoxy, and tert-butoxy. Particular alkoxy are methoxy and ethoxy, most particularly methoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, and trifluoromethyl. The term "perhaloalkyl" denotes an alkyl group where all hydrogen atoms of the alkyl group have been replaced by the same or different halogen atoms. Particular haloalkyl are trifluoromethyl and 2,2,2-trifluoroethyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy and -propoxy, for example 3,3,3-trifluoropropoxy, 2-fluoroethoxy, 2,2,2-trifluoroethoxy, fluoromethoxy, and trifluoromethoxy. The term "perhaloalkoxy" denotes an alkoxy group where all hydrogen atoms of the alkoxy group have been replaced by the same or different halogen atoms.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. "Bicyclic" means consisting of two saturated carbocycles having one or more carbon atom in common. Particular cycloalkyl groups are monocyclic. Examples for monocyclic cycloalkyl are cyclopropyl, cyclobutanyl, cyclopentyl, cyclohexyl and cycloheptyl. Examples for bicyclic cycloalkyl are bicyclo[2.2.1]heptanyl, and bicyclo[2.2.2]octanyl. Particular cycloalkyl are cyclopropyl, cyclobutyl, cyclopentyl, and cyclohexyl, most particularlty cyclopropyl and cyclohexyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "heterocycloalkyl" denotes a monovalent saturated or partly unsaturated mono- or bicyclic ring system of 4 to 9 ring atoms, containing 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, and dihydropyranyl. Particular heterocycloalkyl are oxetanyl, tetrahydrofuranyl, tetrahydrothiophenyl, tetrahydropyranyl, piperazinyl, piperidinyl, morpholinyl, and dioxanyl. Most particular heterocycloalkyl are tetrahydropyranyl and dioxanyl.

The term "aromatic" denotes the conventional idea of aromaticity as defined in the literature, in particular in *IUPAC—Compendium of Chemical Terminology*, 2nd, A. D. McNaught & A. Wilkinson (Eds). Blackwell Scientific Publications, Oxford (1997).

The term "aryl" denotes a monovalent aromatic carbocyclic mono- or bicyclic ring system containing 6 to 10 carbon ring atoms. Examples of aryl moieties include phenyl and naphthyl. Particular aryl is phenyl.

The term "heteroaryl" denotes a monovalent aromatic heterocyclic mono- or bicyclic ring system of 5 to 12 ring atoms, containing 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, and quinoxalinyl. Particular heteroaryl are isoxazolyl, imidazolyl, pyridinyl, 2,3-dihydroindolyl, 2-benzo[1,3]dioxolyl, quinolinyl, chromanyl, and 2,3-dihydrobenzo[1,4]dioxinyl, most particularly isoxazolyl.

The term "oxo" denotes a divalent oxygen atom =O.

The term "active pharmaceutical ingredient" (or "API") denotes the compound in a pharmaceutical composition that has a particular biological activity.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "pharmaceutical composition" (or "composition") denotes a mixture or solution containing a therapeutically effective amount of an active pharmaceutical ingredient together with pharmaceutically acceptable excipients to be administered to a mammal, e.g., a human in need thereof.

The term "half maximal inhibitory concentration" (IC50) denotes the concentration of a particular compound required for obtaining 50% inhibition of a biological process in vitro. IC50 values can be converted logarithmically to pIC50 values (−log IC50), in which higher values indicate exponentially greater potency. The IC50 value is not an absolute value but depends on experimental conditions e.g. concentrations employed. The IC50 value can be converted to an absolute inhibition constant (Ki) using the Cheng-Prusoff equation (Biochem. Pharmacol. (1973) 22:3099).

The term "dissociation constant" (Kd) denotes the propensity of a complex (e.g. between a ligand and a receptor) to dissociate reversibly under equilibrium conditions.

The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgement of the attending medical or veterinary practitioner, and other factors.

The term "treating" or "treatment" of a disease state includes (1) preventing the disease state, i.e. causing the clinical symptoms of the disease state not to develop in a subject that can be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

The term "subject" denotes a vertebrate. In certain embodiments, the vertebrate is a mammal Mammals include humans, non-human primates such as chimpanzees and other apes and monkey species, farm animals such as cattle, horses, sheep, goats, and swine, domestic animals such as rabbits, dogs, and cats, laboratory animals including rodents, such as rats, mice, and guinea pigs. In certain embodiments, a mammal is a human. The term subject does not denote a particular age or sex.

In detail, the present invention provides compounds of formula (I)

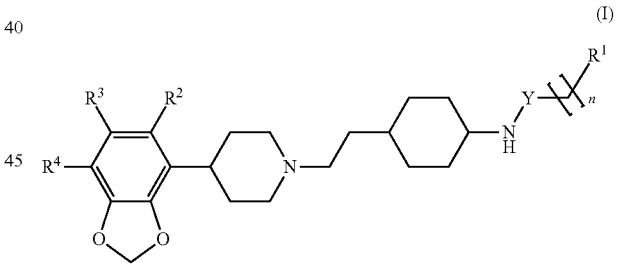

wherein
n is 0, 1, 2 or 3;
Y is —C(O)— or —S(O)$_2$—;
R$^1$ is hydrogen, halogen, cyano, alkyl, haloalkyl, hydroxy, alkoxy, haloalkoxy, cycloalkyl, heterocycloalkyl, aryl, heteroaryl, —NR$^7$R$^8$, —C(O)—NR$^7$R$^8$, or —S(O)$_2$—R$^9$;
wherein alkyl, haloalkyl, and alkoxy are each optionally substituted by one, two or three independent R$^5$; and
wherein cycloalkyl, heterocycloalkyl, aryl, and heteroaryl are each optionally substituted by one, two or three independent R$^6$;
R$^2$, R$^3$, and R$^4$ are each independently hydrogen, halogen, cyano, alkyl, haloalkyl, hydroxy, alkoxy or haloalkoxy;
R$^5$ is cyano, hydroxy, alkoxy, cycloalkyl, heterocycloalkyl, aryl, or heteroaryl, wherein cycloalkyl, heterocycloalkyl, aryl, and heteroaryl are each optionally substituted by one, two or three independent R$^6$;

R⁶ is halogen, cyano, alkyl, haloalkyl, hydroxy, alkoxy, haloalkoxy, oxo, cycloalkyl, heterocycloalkyl, aryl, or heteroaryl;

R⁷ and R⁸ are each independently hydrogen, alkyl, cycloalkyl, cycloalkylalkyl, heterocycloalkyl, heterocycloalkylalkyl, aryl, or heteroaryl;
wherein cycloalkyl, heterocycloalkyl, aryl, and heteroaryl are each optionally substituted by one, two or three independent R¹⁰;

R⁹ is alkyl, cycloalkyl, heterocycloalkyl, aryl, heteroaryl, or —NR⁷R⁸;
wherein cycloalkyl, heterocycloalkyl, aryl, and heteroaryl are each optionally substituted by one, two or three independent R¹¹;

R¹⁰ is halogen, cyano, alkyl, haloalkyl, hydroxy, alkoxy, haloalkoxy, or oxo;

R¹¹ is halogen, cyano, alkyl, haloalkyl, hydroxy, alkoxy, haloalkoxy, or oxo;

and pharmaceutically acceptable salts and esters thereof.

Particular embodiments of present invention are compounds of formula (I) and pharmaceutically acceptable salts thereof and pharmaceutically acceptable esters thereof.

Further, it is to be understood that every embodiment relating to a specific residue n, Y, R¹, R², R³, R⁴, R⁵, R⁶, R⁷ or R⁸ as disclosed herein can be combined with any other embodiment relating to another residue n, Y, R¹, R², R³, R⁴, R⁵, R⁶, R⁷ or R⁸ as disclosed herein.

In one embodiment, the present invention provides compounds of formula (I) wherein
n is 0, 1, 2 or 3;
Y is —C(O)— or —S(O)₂—;
R¹ is hydrogen, cyano, alkyl, haloalkyl, hydroxy, alkoxy, haloalkoxy, cycloalkyl, heterocycloalkyl, aryl, heteroaryl, —NR⁷R⁸, —C(O)—NR⁷R⁸, or —S(O)₂—R⁹;
wherein alkyl, haloalkyl, and alkoxy are each optionally substituted by one, two or three independent R⁵; and
wherein cycloalkyl, heterocycloalkyl, aryl, and heteroaryl are each optionally substituted by one, two or three independent R⁶;
R², R³, and R⁴ are each independently hydrogen, halogen, cyano, alkyl, haloalkyl, hydroxy, alkoxy or haloalkoxy;
R⁵ is cyano, hydroxy, alkoxy, cycloalkyl, heterocycloalkyl, aryl, or heteroaryl, wherein cycloalkyl, heterocycloalkyl, aryl, and heteroaryl are each optionally substituted by one, two or three independent R⁶;
R⁶ is halogen, cyano, alkyl, haloalkyl, hydroxy, alkoxy, haloalkoxy, oxo, cycloalkyl, heterocycloalkyl, aryl, or heteroaryl;
R⁷ and R⁸ are each independently hydrogen, alkyl, cycloalkyl, cycloalkylalkyl, heterocycloalkyl, heterocycloalkylalkyl, aryl, or heteroaryl;
R⁹ is alkyl, cycloalkyl, cycloalkylalkyl, heterocycloalkyl, heterocycloalkylalkyl, aryl, or heteroaryl;
and pharmaceutically acceptable salts and esters thereof.

In one embodiment, the present invention provides compounds of formula (I) wherein
n is 0, 1, 2 or 3;
Y is —C(O)— or —S(O)₂—;
R¹ hydrogen, halogen, cyano, alkyl, haloalkyl, hydroxy, alkoxy, cycloalkyl, heterocycloalkyl, aryl, heteroaryl, —NR⁷R⁸, or —S(O)₂—R⁹;
wherein alkyl, haloalkyl, and alkoxy are each optionally substituted by one, two or three independent R⁵; and
wherein cycloalkyl, heterocycloalkyl, aryl, and heteroaryl are each optionally substituted by one, two or three independent R⁶;
R², R³, and R⁴ are each hydrogen;
R⁵ is hydroxy or alkoxy;
R⁶ is halogen, cyano, alkyl, haloalkyl, hydroxy, alkoxy, oxo, or heterocycloalkyl;
R⁷ and R⁸ are each independently hydrogen, alkyl, or aryl; wherein aryl is optionally substituted by one halogen.
R⁹ is alkyl, heterocycloalkyl, aryl, heteroaryl, or —NR⁷R⁸; wherein heterocycloalkyl, aryl, and heteroaryl are each optionally substituted by one halogen or alkyl;
and pharmaceutically acceptable salts and esters thereof.

A particular embodiment of the present invention provides compounds of formula (I) wherein the two opposing substituents at the central cyclohexyl moiety of the molecular backbone, the amidyl residue and the piperidinyl-ethyl residue, are oriented in trans-configuration.

A particular embodiment of the present invention provides compounds of formula (I')

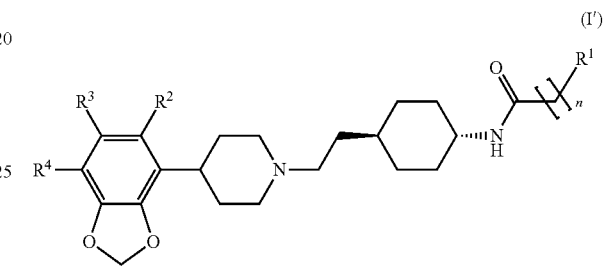

(I')

wherein n, R¹, R², R³ and R⁴ are as defined herein.

A particular embodiment of the present invention provides compounds of formula (I")

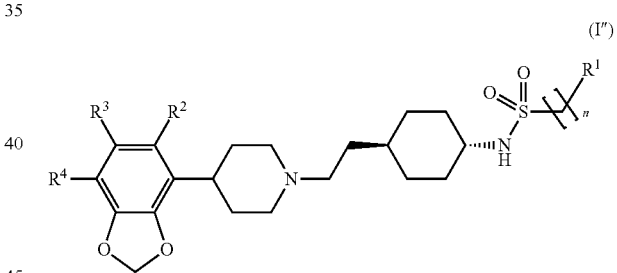

(I")

wherein n, R¹, R², R³ and R⁴ are as defined herein.

In a particular embodiment of the compound of formula (I), n is O.

In a particular embodiment of the compound of formula (I), n is 1.

In a particular embodiment of the compound of formula (I), n is 2.

In a particular embodiment of the compound of formula (I), n is 3.

In a particular embodiment of the compound of formula (I), Y is —C(O)—.

In a particular embodiment of the compound of formula (I), Y is —S(O)₂—.

In a particular embodiment of the compound of formula (I), R¹ is hydrogen, halogen, cyano, alkyl, haloalkyl, hydroxy, alkoxy, cycloalkyl, heterocycloalkyl, aryl, heteroaryl, —NR⁷R⁸, or —S(O)₂—R⁹; wherein alkyl, haloalkyl, and alkoxy are each optionally substituted by one, two or three independent R⁵; and wherein cycloalkyl, heterocycloalkyl, aryl, and heteroaryl are each optionally substituted by one, two or three independent R⁶.

In a particular embodiment of the compound of formula (I), $R^1$ is alkyl, alkoxy, cycloalkyl, heterocycloalkyl, aryl, or heteroaryl; wherein alkyl, and alkoxy are each optionally substituted by one, two or three independent $R^5$; and wherein cycloalkyl, heterocycloalkyl, aryl, and heteroaryl are each optionally substituted by one, two or three independent $R^6$.

In a particular embodiment of the compound of formula (I), $R^1$ is hydrogen, fluoro, cyano, ethyl, hydroxy-ethyl, methoxy-ethyl, isopropyl, hydroxy-isopropyl, isobutyl, hydroxy-isobutyl, sec-butyl, trifluoromethyl, trifluoroethyl, hydroxy-trifluoroethyl, hydroxy, methoxy, ethoxy, cyclopropyl, difluoro-cyclopropyl, trifluoromethyl-cyclopropyl, hydroxy-cyclopropyl, cyclobutyl, chloro-cyclobutyl, hydroxy-cyclobutyl, cyclopentyl, methoxy-cyclopentyl, cyclohexyl, hydroxy-cyclohexyl, methoxy-cyclohexyl, oxetanyl, methyl-oxetanyl, tetrahydrofuranyl, tetrahydrothiophenyl, dioxo-tetrahydrothiophenyl, tetrahydropyranyl, hydroxy-tetrahydropyranyl, piperazinyl, piperidinyl, dioxanyl, phenyl, fluorophenyl, chloro-phenyl, cyano-phenyl, morpholinyl-phenyl, isoxazolyl, methyl-isoxazolyl, pyridinyl, methyl-pyridinyl, 2,3-dihydro-indolyl, 2-benzo[1,3]dioxolyl, quinolinyl, chromanyl, 2,3-dihydrobenzo[1,4]dioxinyl, dimethylamine, chlorophenylamine, methyl-sulfonyl, morpholinyl-sulfonyl, phenyl-sulfonyl, fluorophenyl-sulfonyl, methylimidazolyl-sulfonyl, or dimethylamine-sulfonyl.

In a particular embodiment of the compound of formula (I), $R^1$ is methoxy-ethyl, isopropyl, hydroxy-isopropyl, hydroxy-isobutyl, methoxy, cyclopropyl, hydroxy-cyclopropyl, hydroxy-cyclohexyl, tetrahydropyranyl, dioxanyl, phenyl, or methyl-isoxazolyl.

In a particular embodiment of the compound of formula (I), $R^2$ is hydrogen.

In a particular embodiment of the compound of formula (I), $R^3$ is hydrogen.

In a particular embodiment of the compound of formula (I), $R^4$ is hydrogen.

In a particular embodiment of the compound of formula (I), $R^5$ is hydroxy or alkoxy.

In a particular embodiment of the compound of formula (I), $R^5$ is hydroxy or methoxy.

In a particular embodiment of the compound of formula (I), $R^6$ is halogen, cyano, alkyl, haloalkyl, hydroxy, alkoxy, oxo, or heterocycloalkyl.

In a particular embodiment of the compound of formula (I), $R^6$ is fluoro, chloro, cyano, methyl, trifluoromethyl, hydroxy, methoxy, oxo, or morpholinyl.

In a particular embodiment of the compound of formula (I), $R^6$ is alkyl, hydroxy, or alkoxy.

In a particular embodiment of the compound of formula (I), $R^6$ is methyl, hydroxy, or methoxy.

In a particular embodiment of the compound of formula (I), $R^7$ and $R^8$ are each independently hydrogen, alkyl, or aryl; wherein aryl is optionally substituted by one halogen.

In a particular embodiment of the compound of formula (I), $R^7$ and $R^8$ are each independently hydrogen, methyl, phenyl, or chlorophenyl.

In a particular embodiment of the compound of formula (I), $R^9$ is alkyl, heterocycloalkyl, aryl, heteroaryl, or —$NR^7R^8$; wherein heterocycloalkyl, aryl, and heteroaryl are each optionally substituted by one halogen or alkyl.

In a particular embodiment of the compound of formula (I), $R^9$ is methyl, morpholinyl, phenyl, fluorophenyl, imidazolyl, methylimidazolyl, or dimethylamine.

In a particular embodiment of the compound of formula (I), $R^{19}$ is halogen.

In a particular embodiment of the compound of formula (I), $R^{19}$ is chloro.

In a particular embodiment of the compound of formula (I), $R^H$ is halogen or alkyl.

In a particular embodiment of the compound of formula (I), $R^H$ is fluoro or methyl.

A particular embodiment of the present invention provides compounds of formula (I) as described in the examples as individual compounds as well as pharmaceutically acceptable salts as well as pharmaceutically acceptable esters thereof. Furthermore, the substituents as found in the specific examples described below individually constitute separate particular embodiments of the present invention.

Particular compounds of formula (I) of present invention are those selected from the group consisting of:

Trans-N-{4-[2-(4-Benzo[1,3]dioxol-4-yl-piperidin-1-yl)-ethyl]-cyclohexyl}-acetamide;

Trans-N-{4-[2-(4-Benzo[1,3]dioxol-4-yl-piperidin-1-yl)-ethyl]-cyclohexyl}-3-methoxy-propionamide;

Trans-N-{4-[2-(4-Benzo[1,3]dioxol-4-yl-piperidin-1-yl)-ethyl]-cyclohexyl}-2-[1,4]dioxan-2-yl-acetamide;

Trans-N-{4-[2-(4-Benzo[1,3]dioxol-4-yl-piperidin-1-yl)-ethyl]-cyclohexyl}-2-(S)-[1,4]dioxan-2-yl-acetamide;

Trans-N-{4-[2-(4-Benzo[1,3]dioxol-4-yl-piperidin-1-yl)-ethyl]-cyclohexyl}-2-(R)-[1,4]dioxan-2-yl-acetamide;

Trans-N-{4-[2-(4-Benzo[1,3]dioxol-4-yl-piperidin-1-yl)-ethyl]-cyclohexyl}-2-(tetrahydro-furan-2-yl)-acetamide;

Trans-N-{4-[2-(4-Benzo[1,3]dioxol-4-yl-piperidin-1-yl)-ethyl]-cyclohexyl}-propionamide;

Trans-N-{4-[2-(4-Benzo[1,3]dioxol-4-yl-piperidin-1-yl)-ethyl]-cyclohexyl}-2-cyclopropyl-acetamide;

Trans-N-{4-[2-(4-Benzo[1,3]dioxol-4-yl-piperidin-1-yl)-ethyl]-cyclohexyl}-benzamide;

Trans-N-{4-[2-(4-Benzo[1,3]dioxol-4-yl-piperidin-1-yl)-ethyl]-cyclohexyl}-3,3,3-trifluoro-propionamide;

Trans-N-{4-[2-(4-Benzo[1,3]dioxol-4-yl-piperidin-1-yl)-ethyl]-cyclohexyl}-4,4,4-trifluoro-butyramide;

Trans-N-{4-[2-(4-Benzo[1,3]dioxol-4-yl-piperidin-1-yl)-ethyl]-cyclohexyl}-3,3,3-trifluoro-2-hydroxy-propionamide;

Trans-N-{4-[2-(4-Benzo[1,3]dioxol-4-yl-piperidin-1-yl)-ethyl]-cyclohexyl}-2-methoxy-acetamide;

Trans-N-{4-[2-(4-Benzo[1,3]dioxol-4-yl-piperidin-1-yl)-ethyl]-cyclohexyl}-4-cyano-benzamide;

Trans-N-{4-[2-(4-Benzo[1,3]dioxol-4-yl-piperidin-1-yl)-ethyl]-cyclohexyl}-6-methyl-nicotinamide;

Trans-N-{4-[2-(4-Benzo[1,3]dioxol-4-yl-piperidin-1-yl)-ethyl]-cyclohexyl}-2-(R)-tetrahydro-furan-2-yl-acetamide;

Trans-N-{4-[2-(4-Benzo[1,3]dioxol-4-yl-piperidin-1-yl)-ethyl]-cyclohexyl}-2-(S)-tetrahydro-furan-2-yl-acetamide;

Trans-{4-[2-(4-Benzo[1,3]dioxol-4-yl-piperidin-1-yl)-ethyl]-cyclohexyl}-carbamic acid methyl ester;

Trans-N-{4-[2-(4-Benzo[1,3]dioxol-4-yl-piperidin-1-yl)-ethyl]-cyclohexyl}-2-(3-methyl-isoxazol-5-yl)-acetamide;

Trans-N-{4-[2-(4-Benzo[1,3]dioxol-4-yl-piperidin-1-yl)-ethyl]-cyclohexyl}-2-cyano-acetamide;

Trans-N-{4-[2-(4-Benzo[1,3]dioxol-4-yl-piperidin-1-yl)-ethyl]-cyclohexyl}-2-(1-hydroxy-cyclohexyl)-acetamide;

Trans-N-{4-[2-(4-Benzo[1,3]dioxol-4-yl-piperidin-1-yl)-ethyl]-cyclohexyl}-2-(tetrahydro-pyran-2-yl)-acetamide;

Trans-N-{4-[2-(4-Benzo[1,3]dioxol-4-yl-piperidin-1-yl)-ethyl]-cyclohexyl}-isobutyramide;

Trans-N-{4-[2-(4-Benzo[1,3]dioxol-4-yl-piperidin-1-yl)-ethyl]-cyclohexyl}-3-methyl-butyramide;

Trans-N-{4-[2-(4-Benzo[1,3]dioxol-4-yl-piperidin-1-yl)-ethyl]-cyclohexyl}-butyramide;

Trans-2,2-Difluoro-cyclopropanecarboxylic acid {4-[2-(4-benzo[1,3]dioxol-4-yl-piperidin-1-yl)-ethyl]-cyclohexyl}-amide;

Trans-N-{4-[2-(4-Benzo[1,3]dioxol-4-yl-piperidin-1-yl)-ethyl]-cyclohexyl}-3-methoxy-butyramide;

3-Chloro-cyclobutanecarboxylic acid trans-{4-[2-(4-benzo[1,3]dioxol-4-yl-piperidin-1-yl)-ethyl]-cyclohexyl}-amide;
Trans-N-{4-[2-(4-Benzo[1,3]dioxol-4-yl-piperidin-1-yl)-ethyl]-cyclohexyl}-2-oxetan-3-yl-acetamide;
Trans-N-{4-[2-(4-Benzo[1,3]dioxol-4-yl-piperidin-1-yl)-ethyl]-cyclohexyl}-2-((1R,3R)-3-methoxy-cyclopentyl)-acetamide;
Trans-N-{4-[2-(4-Benzo[1,3]dioxol-4-yl-piperidin-1-yl)-ethyl]-cyclohexyl}-2-(4-hydroxy-tetrahydro-pyran-4-yl)-acetamide;
Trans-N-{4-[2-(4-Benzo[1,3]dioxol-4-yl-piperidin-1-yl)-ethyl]-cyclohexyl}-2-hydroxy-2-methyl-propionamide;
Trans-(S)—N-{4-[2-(4-Benzo[1,3]dioxol-4-yl-piperidin-1-yl)-ethyl]-cyclohexyl}-2-methoxy-propionamide;
Trans-(R)—N-{4-[2-(4-Benzo[1,3]dioxol-4-yl-piperidin-1-yl)-ethyl]-cyclohexyl}-2-methoxy-propionamide;
Trans-N-{4-[2-(4-Benzo[1,3]dioxol-4-yl-piperidin-1-yl)-ethyl]-cyclohexyl}-3-hydroxy-3-methyl-butyramide;
Trans-N-{4-[2-(4-Benzo[1,3]dioxol-4-yl-piperidin-1-yl)-ethyl]-cyclohexyl}-4-chloro-benzamide;
Trans-N-{4-[2-(4-Benzo[1,3]dioxol-4-yl-piperidin-1-yl)-ethyl]-cyclohexyl}-4-fluoro-benzamide;
Trans-(S)—N-{4-[2-(4-Benzo[1,3]dioxol-4-yl-piperidin-1-yl)-ethyl]-cyclohexyl}-3,3,3-trifluoro-2-hydroxy-propionamide;
Trans-(R)—N-{4-[2-(4-Benzo[1,3]dioxol-4-yl-piperidin-1-yl)-ethyl]-cyclohexyl}-3,3,3-trifluoro-2-hydroxy-propionamide;
Trans-N-{4-[2-(4-Benzo[1,3]dioxol-4-yl-piperidin-1-yl)-ethyl]-cyclohexyl}-2-(S)-tetrahydro-pyran-2-yl-acetamide;
Trans-N-{4-[2-(4-Benzo[1,3]dioxol-4-yl-piperidin-1-yl)-ethyl]-cyclohexyl}-2-(R)-tetrahydro-pyran-2-yl-acetamide;
Trans-N-{4-[2-(4-Benzo[1,3]dioxol-4-yl-piperidin-1-yl)-ethyl]-cyclohexyl}-2-(S)-tetrahydro-pyran-3-yl-acetamide;
Trans-N-{4-[2-(4-Benzo[1,3]dioxol-4-yl-piperidin-1-yl)-ethyl]-cyclohexyl}-2-(R)-tetrahydro-pyran-3-yl-acetamide;
Trans-N-{4-[2-(4-Benzo[1,3]dioxol-4-yl-piperidin-1-yl)-ethyl]-cyclohexyl}-3-ethoxy-propionamide;
Trans-N-{4-[2-(4-Benzo[1,3]dioxol-4-yl-piperidin-1-yl)-ethyl]-cyclohexyl}-2-(1-hydroxy-cyclobutyl)-acetamide;
Tetrahydro-furan-2-carboxylic acid-trans-{4-[2-(4-benzo[1,3]dioxol-4-yl-piperidin-1-yl)-ethyl]-cyclohexyl}-amide;
Tetrahydro-furan-3-carboxylic acid-trans-{4-[2-(4-benzo[1,3]dioxol-4-yl-piperidin-1-yl)-ethyl]-cyclohexyl}-amide;
Tetrahydro-pyran-4-carboxylic acid-trans-{4-[2-(4-benzo[1,3]dioxol-4-yl-piperidin-1-yl)-ethyl]-cyclohexyl}-amide;
1-Hydroxy-cyclopropanecarboxylic acid-trans-{4-[2-(4-benzo[1,3]dioxol-4-yl-piperidin-1-yl)-ethyl]-cyclohexyl}-amide;
Trifluoromethyl-cyclopropanecarboxylic acid-trans-{4-[2-(4-benzo[1,3]dioxol-4-yl-piperidin-1-yl)-ethyl]-cyclohexyl}-amide;
Trans-N-{4-[2-(4-Benzo[1,3]dioxol-4-yl-piperidin-1-yl)-ethyl]-cyclohexyl}-2-methyl-butyramide;
1,1-Dioxo-tetrahydro-thiophene-3-carboxylic acid-trans-{4-[2-(4-benzo[1,3]dioxol-4-yl-piperidin-1-yl)-ethyl]-cyclohexyl}-amide;
Trans-N-{4-[2-(4-Benzo[1,3]dioxol-4-yl-piperidin-1-yl)-ethyl]-cyclohexyl}-2-(tetrahydro-pyran-4-yl)-acetamide;
Cyclobutanecarboxylic acid-trans-{4-[2-(4-benzo[1,3]dioxol-4-yl-piperidin-1-yl)-ethyl]-cyclohexyl}-amide;
Trans-N-{4-[2-(4-Benzo[1,3]dioxol-4-yl-piperidin-1-yl)-ethyl]-cyclohexyl}-2-methanesulfonyl-acetamide;
Trans-N-{4-[2-(4-Benzo[1,3]dioxol-4-yl-piperidin-1-yl)-ethyl]-cyclohexyl}-4-morpholin-4-yl-benzamide;
Quinoline-4-carboxylic acid-trans-N-{4-[2-(4-benzo[1,3]dioxol-4-yl-piperidin-1-yl)-ethyl]-cyclohexyl}-amide;
2,3-Dihydro-benzo[1,4]dioxine-6-carboxylic acid-trans-N-{4-[2-(4-benzo[1,3]dioxol-4-yl-piperidin-1-yl)-ethyl]-cyclohexyl}-amide;
2-Benzo[1,3]dioxol-5-yl-trans-N-{4-[2-(4-benzo[1,3]dioxol-4-yl-piperidin-1-yl)-ethyl]-cyclohexyl}-acetamide;
Chroman-3-carboxylic acid-trans-N-{4-[2-(4-benzo[1,3]dioxol-4-yl-piperidin-1-yl)-ethyl]-cyclohexyl}-amide;
1-Methyl-piperidine-4-carboxylic acid-trans-N-{4-[2-(4-benzo[1,3]dioxol-4-yl-piperidin-1-yl)-ethyl]-cyclohexyl}-amide;
3-Methyl-oxetane-3-carboxylic acid-trans-N-{4-[2-(4-benzo[1,3]dioxol-4-yl-piperidin-1-yl)-ethyl]-cyclohexyl}-amide;
Trans-N-{4-[2-(4-Benzo[1,3]dioxol-4-yl-piperidin-1-yl)-ethyl]-cyclohexyl}-2-(4-methoxy-cyclohexyl)-acetamide;
(R)-trans-N-{4-[2-(4-Benzo[1,3]dioxol-4-yl-piperidin-1-yl)-ethyl]-cyclohexyl}-2-hydroxy-propionamide;
Trans-N-{4-[2-(4-Benzo[1,3]dioxol-4-yl-piperidin-1-yl)-ethyl]-cyclohexyl}-2-hydroxy-acetamide;
1-Hydroxy-cyclohexanecarboxylic acid-trans-N-{4-[2-(4-benzo[1,3]dioxol-4-yl-piperidin-1-yl)-ethyl]-cyclohexyl}-amide;
1-Methoxy-cyclohexanecarboxylic acid-trans-N-{4-[2-(4-benzo[1,3]dioxol-4-yl-piperidin-1-yl)-ethyl]-cyclohexyl}-amide;
Trans-N-{4-[2-(4-Benzo[1,3]dioxol-4-yl-piperidin-1-yl)-ethyl]-cyclohexyl}-2-(4-methylpiperazin-1-yl)-acetamide;
Trans-N-{4-[2-(4-Benzo[1,3]dioxol-4-yl-piperidin-1-yl)-ethyl]-cyclohexyl}-methanesulfonamide;
Trans-N-{4-[2-(4-Benzo[1,3]dioxol-4-yl-piperidin-1-yl)-ethyl]-cyclohexyl}-benzenesulfonamide;
N-trans-{4-[2-(4-Benzo[1,3]dioxol-4-yl-piperidin-1-yl)-ethyl]-cyclohexyl}-4-fluoro-benzenesulfonamide;
1-Methyl-1H-imidazole-4-sulfonic acid-trans-N-{4-[2-(4-benzo[1,3]dioxol-4-yl-piperidin-1-yl)-ethyl]-cyclohexyl}-amide;
Trans-N-{4-[2-(4-Benzo[1,3]dioxol-4-yl-piperidin-1-yl)-ethyl]-cyclohexyl}-2,2,2-trifluoro-acetamide;
2,3-Dihydro-indole-1-carboxylic acid N-trans-{4-[2-(4-benzo[1,3]dioxol-4-yl-piperidin-1-yl)-ethyl]-cyclohexyl}-amide;
N-Trans-3-{4-[2-(4-Benzo[1,3]dioxol-4-yl-piperidin-1-yl)-ethyl]-cyclohexyl}-1,1-dimethyl-urea;
Trans-N-{4-[2-(4-Benzo[1,3]dioxol-4-yl-piperidin-1-yl)-ethyl]-cyclohexyl}-2-fluoro-acetamide;
N-trans-1-{4-[2-(4-Benzo[1,3]dioxol-4-yl-piperidin-1-yl)-ethyl]-cyclohexyl}-3-(4-chloro-phenyl)-urea;
Trans-N-{4-[2-(4-benzo[1,3]dioxol-4-yl-piperidin-1-yl)-ethyl]-cyclohexyl}-N,N-dimethyl-sulfamide;
Morpholine-4-sulfonic acid-Trans-N-{4-[2-(4-benzo[1,3]dioxol-4-yl-piperidin-1-yl)-ethyl]-cyclohexyl}-amide; and
pharmaceutically acceptable salts and esters thereof.

Particular compounds of formula (I) of present invention are those selected from the group consisting of:
Trans-N-{4-[2-(4-Benzo[1,3]dioxol-4-yl-piperidin-1-yl)-ethyl]-cyclohexyl}-2-(S)-[1,4]dioxan-2-yl-acetamide;
Trans-N-{4-[2-(4-Benzo[1,3]dioxol-4-yl-piperidin-1-yl)-ethyl]-cyclohexyl}-2-(R)-[1,4]dioxan-2-yl-acetamide;
Trans-N-{4-[2-(4-Benzo[1,3]dioxol-4-yl-piperidin-1-yl)-ethyl]-cyclohexyl}-2-cyclopropyl-acetamide;
Trans-N-{4-[2-(4-Benzo[1,3]dioxol-4-yl-piperidin-1-yl)-ethyl]-cyclohexyl}-benzamide;
Trans-N-{4-[2-(4-Benzo[1,3]dioxol-4-yl-piperidin-1-yl)-ethyl]-cyclohexyl}-2-methoxy-acetamide;

Trans-N-{4-[2-(4-Benzo[1,3]dioxol-4-yl-piperidin-1-yl)-ethyl]-cyclohexyl}-2-(3-methyl-isoxazol-5-yl)-acetamide;
Trans-N-{4-[2-(4-Benzo[1,3]dioxol-4-yl-piperidin-1-yl)-ethyl]-cyclohexyl}-2-(1-hydroxy-cyclohexyl)-acetamide;
Trans-N-{4-[2-(4-Benzo[1,3]dioxol-4-yl-piperidin-1-yl)-ethyl]-cyclohexyl}-2-(tetrahydro-pyran-2-yl)-acetamide;
Trans-N-{4-[2-(4-Benzo[1,3]dioxol-4-yl-piperidin-1-yl)-ethyl]-cyclohexyl}-isobutyramide;
Trans-N-{4-[2-(4-Benzo[1,3]dioxol-4-yl-piperidin-1-yl)-ethyl]-cyclohexyl}-2-hydroxy-2-methyl-propionamide;
Trans-(R)—N-{4-[2-(4-Benzo[1,3]dioxol-4-yl-piperidin-1-yl)-ethyl]-cyclohexyl}-2-methoxy-propionamide;
Trans-N-{4-[2-(4-Benzo[1,3]dioxol-4-yl-piperidin-1-yl)-ethyl]-cyclohexyl}-3-hydroxy-3-methyl-butyramide;
Trans-N-{4-[2-(4-Benzo[1,3]dioxol-4-yl-piperidin-1-yl)-ethyl]-cyclohexyl}-2-(R)-tetrahydro-pyran-2-yl-acetamide;
Trans-N-{4-[2-(4-Benzo[1,3]dioxol-4-yl-piperidin-1-yl)-ethyl]-cyclohexyl}-(R)-tetrahydro-pyran-3-yl-acetamide;
1-Hydroxy-cyclopropanecarboxylic acid-trans-{4-[2-(4-benzo[1,3]dioxol-4-yl-piperidin-1-yl)-ethyl]-cyclohexyl}-amide; and
pharmaceutically acceptable salts and esters thereof.

The invention further provides a process for the manufacture of compounds of formula (I) as defined above which comprises:
a) the reaction of a compound of formula (V)

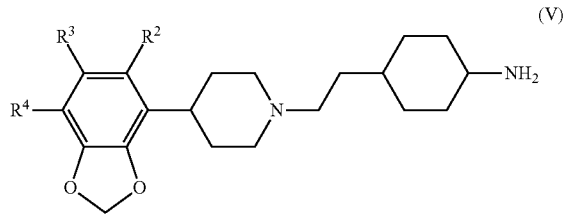

(V)

with a compound of formula $R^1(CH_2)_nC(O)OH$, $R^1(CH_2)_nC(O)OR$ or $R^1(CH_2)_nS(O)_2Cl$, wherein n, $R^1$, $R^2$, $R^3$ and $R^4$ are as defined above and R is alkyl; or
b) the reaction of a compound of formula (II)

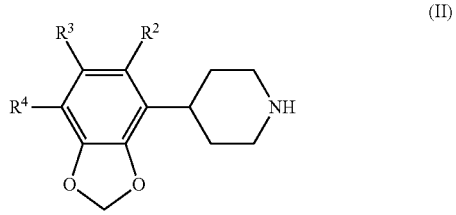

(II)

with a compound of formula (VI)

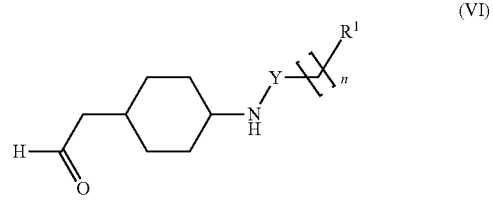

(VI)

wherein n, Y, $R^1$, $R^2$, $R^3$ and $R^4$ are as defined above.

Particularly, compounds of formula (I) can be prepared following standard methods in accordance with Schemes 1 or 2.

According to Scheme 1, in a first step, a compound of formula (II) is reacted with an aldehyde of formula (III) under reductive amination conditions such as for example the use of sodium triacetoxyborohydride (Na(AcO)$_3$BH) in a solvent such as 1,2-dichloroethane in the presence of methanol (MeOH) or an acid such as acetic acid (AcOH) to give a compound of formula (IV). The amino moiety of aldehyde (III) is protected with an amino-protecting group such as a Boc moiety. In a second step, compounds of formula (IV) are deprotected to give compounds of formula (V). In such cases where the amino-protecting group is a Boc functionality, compounds of formula (IV) can be reacted with an acid as for example HCl in an appropriate solvent mixture such as ethylacetate (AcOEt) and MeOH to give primary amines isolated as the HCl salts (V).

Compounds of formula (V) can be reacted in a third step with a number of different nucleophiles to obtain compounds of formula (I). For instance reaction of compounds of formula (V) with a carboxylic acid of general structure $R^1(CH_2)_nC(O)OH$ in the presence of a coupling agent such as O-(benzotriazol-1-yl)-N,N,N',N'-tetramethyluronium tetrafluoroborate (TBTU) and a base such as Hunig's base (N,N-Diisopropylethylamine, DIPEA) in a solvent such as dimethylformamide (DMF) leads to compounds of formula (I'). In some instances carboxylic acids of general structure $R^1(CH_2)_nC(O)OH$ or their salts can be prepared by saponification of an ester of formula $R^1(CH_2)_nC(O)OR$, wherein R is alkyl, with a reagent such as a base like LiOH or mild reagents like potassium trimethylsilanolate (KOSiMe$_3$) in a solvent such as dichloromethane (DCM) followed by full evaporation of all solvent and direct use of the crude in the amide coupling step described above to obtain compounds of formula (I').

Yet in another instance, compounds of formula (V) can be reacted with an appropriate reagent of general structure $R^1(CH_2)_nS(O)_2Cl$ in the presence of a base such as triethylamine (Et$_3$N) in a solvent such as DCM to obtain compounds of formula (I'').

Scheme 1.

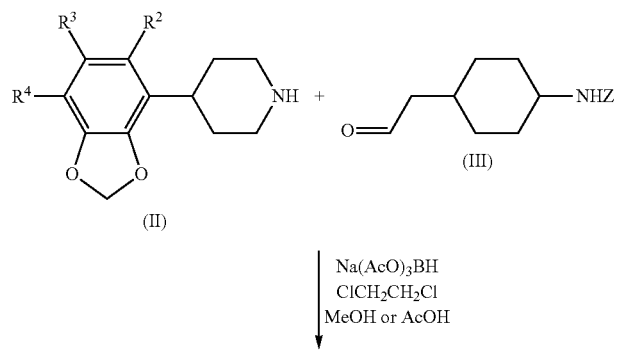

Na(AcO)$_3$BH
ClCH$_2$CH$_2$Cl
MeOH or AcOH

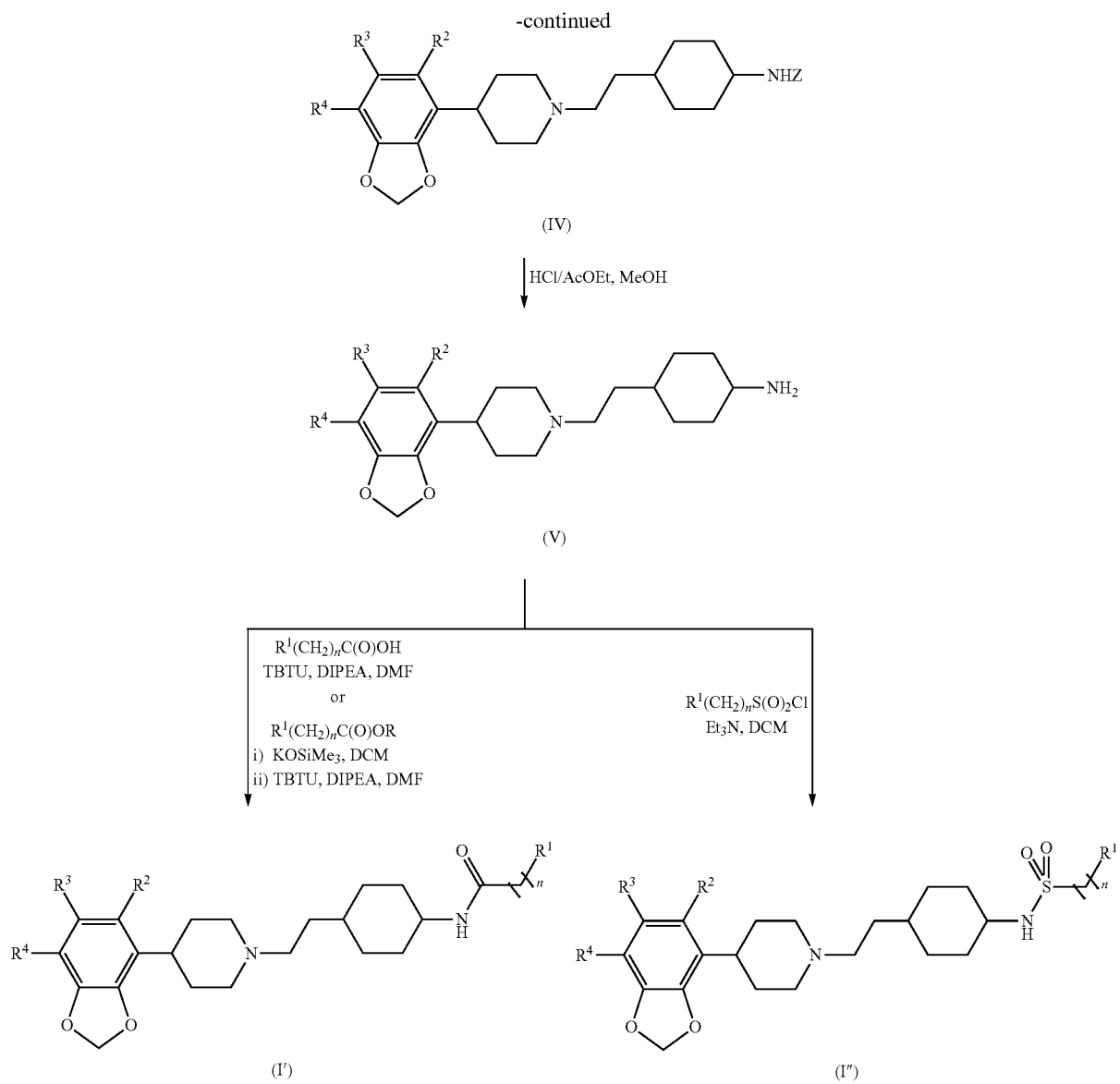

wherein n, $R^1$, $R^2$, $R^3$ and $R^4$ are as defined above, Z is an amino-protecting group and R is alkyl.

Derivatization at the primary amine does not necessarily need to be carried out in a last step, but can occur already prior to the reductive amination step, thus avoiding the use of an amino-protecting group. According to Scheme 2, the reductive amination of a compound of formula (II) with an aldehyde of formula (VI) under conditions well known to the person skilled in the art, will directly lead to an amide of formula (I). An example for appropriate conditions for this step is the use of Na(AcO)$_3$BH in a solvent such as 1,2-dichloroethane in the presence or not of MeOH or an acid such as AcOH. Methods to generate compounds of formula (VI) have been described (e.g. WO 2007/093540).

Scheme 2.

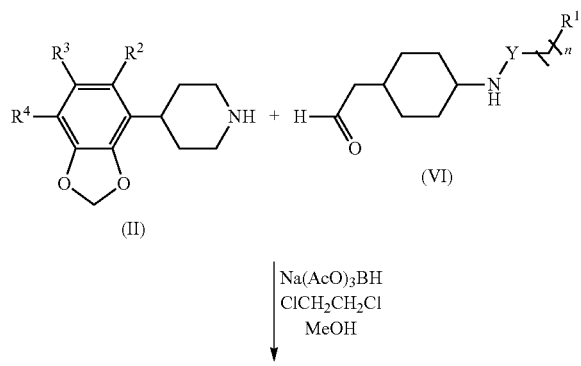

-continued

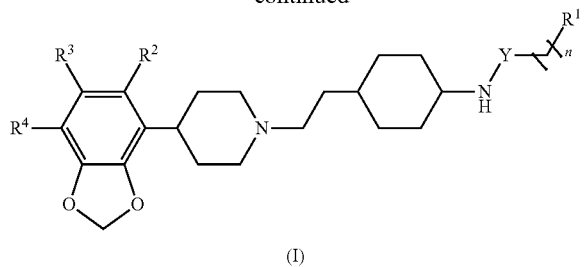

(I)

wherein n, Y, R¹, R², R³ and R⁴ are as defined above.

In some occasions the starting material (II) might need to be synthesized as it is not commercially available. According to Scheme 3, compounds of formula (II) can be obtained from compounds of formula (VII), wherein X is halogen, particularly bromo, by coupling with a compound of formula (VIII) or similar boronic derivative, wherein Z is an amino-protecting group, particularly Boc. The coupling between the compound of formula (VII) and the compound of formula (VIII) is performed under conditions well known to the person skilled in the art to obtain a compound of formula (IX). For instance under Suzuki conditions using a catalyst such as palladium (II) acetate in presence of a ligand, particularly triphenylphosphine, in the presence of a base, particularly potassium bicarbonate, in a solvent, particularly 1,2-dimethoxyethane. Other coupling conditions are well known to person skilled in the art. In a second step, compounds of formula (IX), where Z is an amino-protecting group, particularly Boc, can be reacted with an acid, particularly HCl, in an appropriate solvent mixture, particularly dioxane and MeOH, to give primary amines of formula (X), isolated as the corresponding salts, particularly as the HCl salts. Reduction of the double bond of compounds of formula (X) can be performed using Pd/C to obtain the desired benzodioxole piperidines of formula (II).

The corresponding salts of compounds of formula (I) with acids can be obtained by standard methods known to the person skilled in the art, e.g. by dissolving the compound of formula (I) in a suitable solvent such as e.g. dioxan or tetrahydrofuran (THF) and adding an appropriate amount of the corresponding acid. The products can usually be isolated by filtration or by chromatography.

The conversion of compounds of formula (I) into pharmaceutically acceptable esters can be carried out e.g. by treatment of a suitable hydroxy-group present in the molecule with a suitable carboxylic acid using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU).

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

The present invention also provides compounds of formula (I) as defined above, when prepared by a process as described above.

Another embodiment provides pharmaceutical compositions or medicaments containing the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of adminis- Scheme 3.

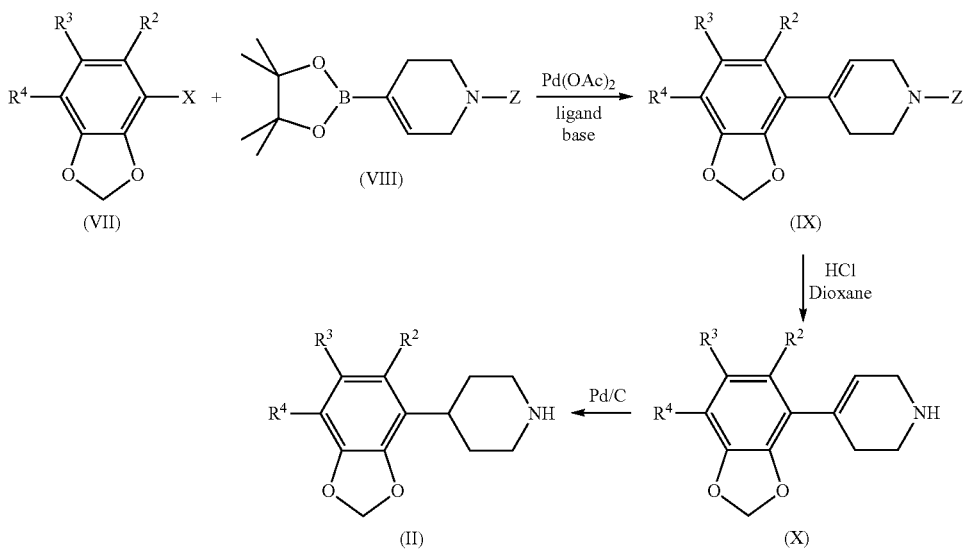

wherein R², R³, and R⁴ are as defined above, X is halogen, Z is an amino-protecting group.

tration, the scheduling of administration, and other factors known to medical practitioners.

The compounds of the invention can be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention can be administered in any convenient administrative form, e.g., tablets, powders, capsules, solutions, dispersions, suspensions, syrups, sprays, suppositories, gels, emulsions, patches, etc. Such compositions can contain components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, Handbook of Pharmaceutical Excipients (2005) Pharmaceutical Press, Chicago. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.1 to 1000 mg per person of a compound of general formula (I) should be appropriate, although the above upper limit can also be exceeded when necessary.

An example of a suitable oral dosage form is a tablet which comprises about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 µm filter, to remove impurities and contaminants.

As described above, the novel compounds of the present invention and their pharmaceutically acceptable salts and esters possess valuable pharmacological properties and are dual modulators of the $5\text{-HT}_{2A}$ and $D_3$ receptors. The compounds of the present invention can therefore be used, either alone or in combination with other drugs, for the treatment or prevention of diseases which are modulated by ligands of the $5\text{-HT}_{2A}$ or $D_3$ receptors. These diseases include, but are not limited to, psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions.

The invention therefore also provides pharmaceutical compositions which comprises a compound as defined above and a pharmaceutically acceptable excipient.

The invention likewise embraces compounds as described above for use as therapeutically active substances, especially as therapeutically active substances for the treatment or prevention of diseases which are related to the $5\text{-HT}_{2A}$ or $D_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions.

In another embodiment, the invention provides a method for the treatment or prevention of diseases which are related to the $5\text{-HT}_{2A}$ or $D_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions, which method comprises administering a compound as defined above to a human being or animal.

The invention also embraces the use of compounds as defined above for the treatment or prevention of diseases which are related to the $5\text{-HT}_{2A}$ or $D_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions.

The invention also provides the use of compounds as described above for the preparation of medicaments for the treatment or prevention of diseases which are related to the $5\text{-HT}_{2A}$ or $D_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions. Such medicaments comprise a compound as described above.

Particularly, compounds of present invention can be used in the treatment or prevention of psychotic disorders including schizophrenia as well as positive, negative and/or cognitive symptoms associated with schizophrenia.

The invention will be more fully understood by reference to the following examples. They should not, however, be construed as limiting the scope of the invention.

INTERMEDIATES

Intermediate A

Trans-4-[2-(4-Benzo[1,3]dioxol-4-yl-piperidin-1-yl)-ethyl]-cyclohexylamine hydrochloride

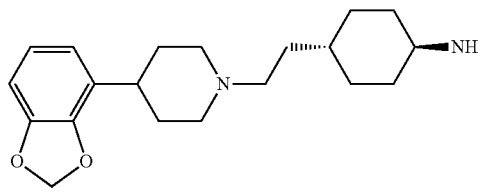 [SMILES: N[C@H]1CC[C@H](CCN2CCC(c3cccc4c3OCO4)CC2)CC1]

Step A: 4-Benzo[1,3]dioxol-4-yl-3,6-dihydro-2H-pyridine-1-carboxylic acid tert-butyl ester Tert-butyl 4-(4,4,5,5-tetramethyl-1,3,2-dioxaborolan-2-yl)-5,6-dihydropyridine-1(2H)-carboxylate (1.62 g, 5.22 mmol) was added to a solution of 4-bromobenzo[d][1,3]dioxole (1 g, 4.97 mmol) in 1,2-Dimethoxyethane (45.0 ml) and Na$_2$CO$_3$ 2M (8.28 ml, 16.6 mmol). The resulting suspension was degassed using a stream of argon in an ultrasonic bath during 5 min. Then triphenylphosphine (261 mg, 995 μmol) and palladium (II) acetate (112 mg, 497 μmol) was added and the reaction mixture was stirred over night at 85° C. The reaction was cooled to rt, diluted with 40 mL of water and the mixture extracted with ethyl acetate (3×50 mL). The organic layers were dried over MgSO$_4$ and concentrated under vacuum. The crude material was purified by flash chromatography (silica gel, 50 g, 0% to 50% EtOAc in heptane) to yield 4-Benzo[1,3]dioxol-4-yl-3,6-dihydro-2H-pyridine-1-carboxylic acid tert-butyl ester as a yellowish liquid (1.22 g, 80.8%). MS (ISP) m/z=304.4 [(M+H)$^+$].

Step B: 4-Benzo[1,3]dioxol-4-yl-1,2,3,6-tetrahydropyridine hydrochloride

In a 50 mL flask, 4-Benzo[1,3]dioxol-4-yl-3,6-dihydro-2H-pyridine-1-carboxylic acid tert-butyl ester (1.22 g, 4.02 mmol was combined with dichloromethane (20 ml) to give a colorless solution. Hydrochloric acid solution, 4M in dioxane (10.1 ml, 40.2 mmol) was added and the reaction mixture was stirred for 4 hours at room temperature. 15 ml of diisoproylether were added and the mixture was stirred for 5 min at 0° C. The precipitate was collected by filtration, washed with 2 ml of diisopropylether and dried to yield the title compound as a white solid (0.820 grs, 85%). MS (ISP) m/z=204.2[(M+H)$^+$].

Step C: 4-Benzo[1,3]dioxol-4-yl-piperidine

Pd/C 10% (169 mg, 159 μmol,) was added to a solution of 4-(benzo[1,3]dioxol-4-yl)-1,2,3,6-tetrahydropyridine hydrochloride (760 mg, 3.17 mmol) and ammonium formate (1.00 g, 15.9 mmol) in methanol (28.8 ml) under argon. After refluxing for 60 min the reaction mixture was cooled to room temperature, filtrated and concentrated under reduced pressure. Saturated sodium bicarbonate solution was added to the residue and the mixture was extracted with dichloromethane (3×25 mL). The organic layers were dried over MgSO$_4$ and concentrated in vacuo to yield the title compound as a white solid (0.654 grs, 100%). MS (ISP) m/z=206.0[(M+H)$^+$].

Step D: Trans-{4-[2-(4-Benzo[1,3]dioxol-4-yl-piperidin-1-yl)-ethyl]-cyclohexyl}-carbamic acid tert-butyl ester To a stirred solution of 4-Benzo[1,3]dioxol-4-yl-piperidine (0.680 g, 3.31 mmol,) in dichloromethane (35 ml) and methanol (1 ml) was added at room temperature commercially available trans-tert-butyl-4-(2-oxoethyl)-cyclohexylcarbamate (1.04 g, 4.31 mmol) and the solution was allowed to stir for 120 min. Sodium triacetoxyboron hydride (1.26 g, 5.96 mmol) was added portion wise and the mixture was allowed to stir for 16 h at room temperature. The solution was poured into saturated sodium bicarbonate solution (15 ml) and extracted with dichloromethane (2×20 ml). The combined organic layers were dried (MgSO$_4$) and evaporated. The crude material was purified by flash chromatography on silica gel The crude material was purified by flash chromatography (methanol in dichloromethane 0-10%) to yield trans-{4-[2-(4-Benzo[1,3]dioxol-4-yl-piperidin-1-yl)-ethyl]-cyclohexyl}-carbamic acid tert-butyl ester as a white solid (1.43 g, 74%), MS (ISP) m/z=431.5 [(M+H)$^+$].

Step E: Trans-4-[2-(4-Benzo[1,3]-dioxol-4-yl-piperidin-1-yl)-ethyl]-cyclohexylamine hydrochloride To a mixture of trans-{4-[2-(4-Benzo[1,3]dioxol-4-yl-piperidin-1-yl)-ethyl]-cyclohexyl}-carbamic acid tert-butyl ester (1.06 g, 2.46 mmol,) in dichloromethane (15 ml) was added at room temperature hydrochloric acid solution (4M in dioxane, 6.15 ml, 24.6 mmol,) and the mixture was allowed to stir for 4 h, the solvent was evaporated, diisopropyl ether (15 ml) were added and the mixture was allowed to stir for 10 min at room temperature. The precipitate was collected by filtration, washed with diisopropyl ether and dried to yield the title compound as a white solid (0.954, 100%), MS m/z=330.23 [(M)$^+$].

EXAMPLES

Example 1

Trans-N-{4-[2-(4-Benzo[1,3]dioxol-4-yl-piperidin-1-yl)-ethyl]-cyclohexyl}-acetamide

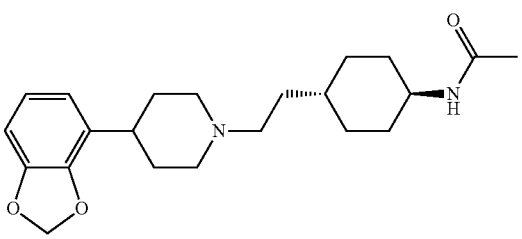 [SMILES: CC(=O)N[C@H]1CC[C@H](CCN2CCC(c3cccc4c3OCO4)CC2)CC1]

To a stirred mixture of Trans-4-[2-(4-Benzo[1,3]dioxol-4-yl-piperidin-1-yl)-ethyl]-cyclohexylamine hydrochloride (intermediate A) (50 mg, 0.136 mmol) in DMF (0.8 ml) was added N,N-diisopropylethylamine (62 mg, 0.0833 ml, 0.477 mmol), acetic acid (9.82 mg, 9.35 µl, 0.164 mmol) and TBTU (52.4 mg, 0.164 mmol). The mixture was allowed to stir at room temperature for 4 h and poured into ice/water (0.5 ml) The crude reaction mixture was concentrated in vacuo. The reaction mixture was solved with sat NaHCO3 (1×10 mL). and extracted with dichloromethane (3×20 mL). The organic layers were dried over MgSO$_4$ and concentrated in vacuo. The crude material was purified by flash chromatography (silica gel, 10 g, 0% to 20% MeOH in dichloromethane) to yield the title compound as an white solid (31 mg, 61%), MS (ISP) m/z=373.5 [(M+H)$^+$].

Example 2

Trans-N-{4-[2-(4-Benzo[1,3]dioxol-4-yl-piperidin-1-yl)-ethyl]-cyclohexyl}-3-methoxy-propionamide

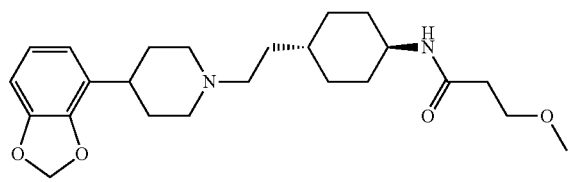 [SMILES: COCCC(=O)N[C@H]1CC[C@H](CCN2CCC(c3cccc4c3OCO4)CC2)CC1]

The title compound, white solid (34.2 mg, 60.3%), MS (ISP) m/z=417.5 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (50 mg, 0.136 mmol) and 3-methoxypropionic acid.

Example 3

Trans-N-{4-[2-(4-Benzo[1,3]dioxol-4-yl-piperidin-1-yl)-ethyl]-cyclohexyl}-2-[1,4]dioxan-2-yl-acetamide

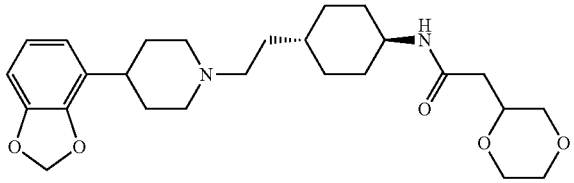 [SMILES: O=C(CC1COCCO1)N[C@H]1CC[C@H](CCN2CCC(c3cccc4c3OCO4)CC2)CC1]

The title compound, white solid (28.4 mg, 45.4%), MS (ISP) m/z=459.5 [(M+H)$^+$], was prepared in accordance with the general method of example 1 Trans-4-[2-(4-Benzo[1,3]dioxol-4-yl-piperidin-1-yl)-ethyl]-cyclohexylamine hydrochloride (intermediate A) (50 mg, 0.136 mmol) and rac-(1,4-dioxan-2-yl)-acetic acid obtained from saponification of the racemic [1,4]Dioxan-2-yl-acetic acid ethyl ester prepared as reported in Tetrahedron Vol. 45, 1989, pp. 69-76.

Example 4

Trans-N-{4-[2-(4-Benzo[1,3]dioxol-4-yl-piperidin-1-yl)-ethyl]-cyclohexyl}-2-(S) or (R)-[1,4]dioxan-2-yl-acetamide

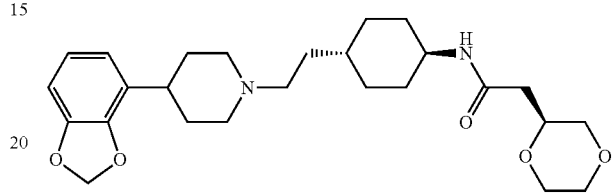

The title compound, white solid (21 mg, 57.3%), MS (ISP) m/z=459.6 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and (S) or (R)-2-(1,4-dioxan-2-yl)acetic acid obtained from chiral separation of rac-[1,4]Dioxan-2-yl-acetic acid benzyl ester (using a Chiralpak AD column with 25% of EtOH in heptane) and hydrogenation to remove the benzyl ester.

Example 5

Trans-N-{4-[2-(4-Benzo[1,3]dioxol-4-yl-piperidin-1-yl)-ethyl]-cyclohexyl}-2-(R) or (S)-[1,4]dioxan-2-yl-acetamide

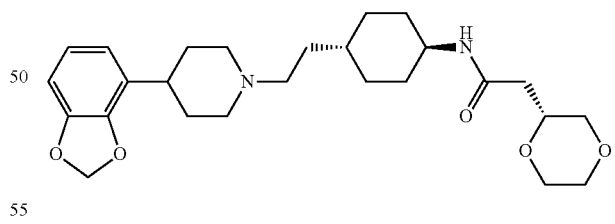

The title compound, white solid (21.3 mg, 58%), MS (ISP) m/z=459.3 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and (S) or (R)-2-(1,4-dioxan-2-yl)acetic acid obtained from chiral separation of rac-[1,4]Dioxan-2-yl-acetic acid benzyl ester (using a Chiralpak AD column with 25% of EtOH in heptane) and hydrogenation to remove the benzyl ester.

Example 6

Trans-N-{4-[2-(4-Benzo[1,3]dioxol-4-yl-piperidin-1-yl)-ethyl]-cyclohexyl}-2-(tetrahydro-furan-2-yl)-acetamide

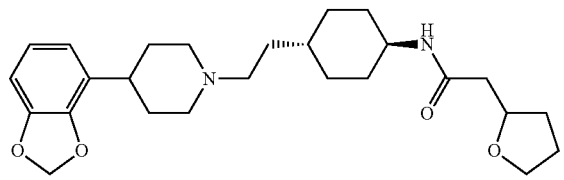 [SMILES: O=C(CC1CCCO1)N[C@H]1CC[C@H](CCN2CCC(c3cccc4c3OCO4)CC2)CC1]

The title compound, white solid (9 mg, 25%), MS (ISP) m/z=443.5 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and 2-(tetrahydrofuran-2-yl)acetic acid.

Example 7

Trans-N-{4-[2-(4-Benzo[1,3]dioxol-4-yl-piperidin-1-yl)-ethyl]-cyclohexyl}-propionamide

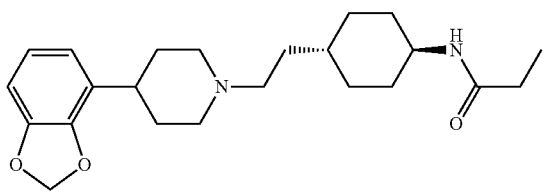 [SMILES: CCC(=O)N[C@H]1CC[C@H](CCN2CCC(c3cccc4c3OCO4)CC2)CC1]

The title compound, white solid (17.9 mg, 57.9%), MS (ISP) m/z=387.4 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and propionic acid.

Example 8

Trans-N-{4-[2-(4-Benzo[1,3]dioxol-4-yl-piperidin-1-yl)-ethyl]-cyclohexyl}-2-cyclopropyl-acetamide

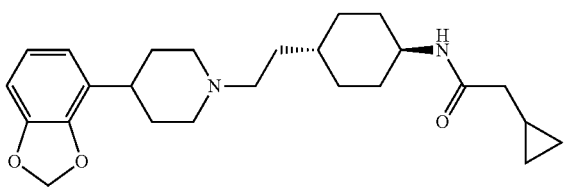 [SMILES: O=C(CC1CC1)N[C@H]1CC[C@H](CCN2CCC(c3cccc4c3OCO4)CC2)CC1]

The title compound, white solid (22.4 mg, 67.9%), MS (ISP) m/z=413.5 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and 2-cyclopropylacetic acid.

Example 9

Trans-N-{4-[2-(4-Benzo[1,3]dioxol-4-yl-piperidin-1-yl)-ethyl]-cyclohexyl}-benzamide

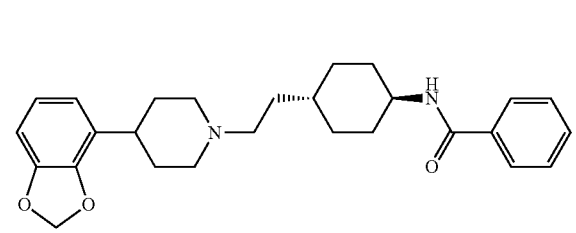 [SMILES: O=C(N[C@H]1CC[C@H](CCN2CCC(c3cccc4c3OCO4)CC2)CC1)c1ccccc1]

The title compound, white solid (24.1 mg, 69.4%), MS (ISP) m/z=435.4 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and benzoic acid.

Example 10

Trans-N-{4-[2-(4-Benzo[1,3]dioxol-4-yl-piperidin-1-yl)-ethyl]-cyclohexyl}-3,3,3-trifluoro-propionamide

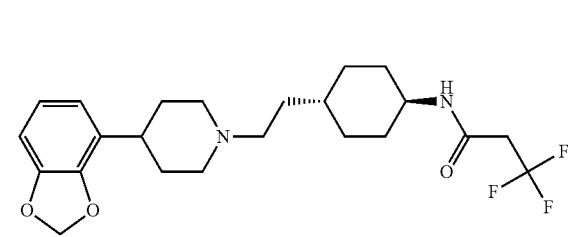 [SMILES: O=C(CC(F)(F)F)N[C@H]1CC[C@H](CCN2CCC(c3cccc4c3OCO4)CC2)CC1]

The title compound, white solid (17.4 mg, 49.4%), MS (ISP) m/z=441.0 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and 3,3,3-trifluoropropanoic acid.

Example 11

Trans-N-{4-[2-(4-Benzo[1,3]dioxol-4-yl-piperidin-1-yl)-ethyl]-cyclohexyl}-4,4,4-trifluoro-butyramide

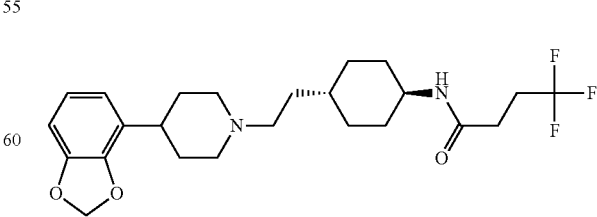

The title compound, white solid (12.8 mg, 35.2%), MS (ISP) m/z=455.4 [(M+H)⁺], was prepared in accordance with the general method of example 1 from Trans-4-[2-(4-Benzo

[1,3]dioxol-4-yl-piperidin-1-yl)-ethyl]-cyclohexylamine hydrochloride (intermediate A) (29.4 mg, 0.080 mmol) and 4,4,4-trifluorobutanoic acid

Example 12

Trans-N-{4-[2-(4-Benzo[1,3]dioxol-4-yl-piperidin-1-yl)-ethyl]-cyclohexyl}-3,3,3-trifluoro-2-hydroxy-propionamide

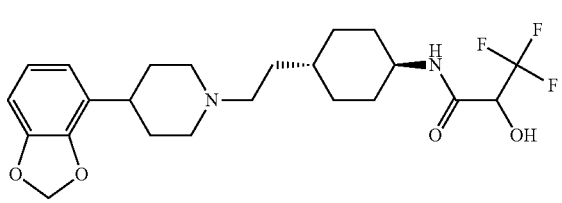 [SMILES: O=C(N[C@H]1CC[C@H](CCN2CCC(c3cccc4c3OCO4)CC2)CC1)C(O)C(F)(F)F]

The title compound, white solid (6.2 mg, 17%), MS (ISP) m/z=457.4 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and 3,3,3-trifluoro-2-hydroxypropanoic acid

Example 13

Trans-N-{4-[2-(4-Benzo[1,3]dioxol-4-yl-piperidin-1-yl)-ethyl]-cyclohexyl}-2-methoxy-acetamide

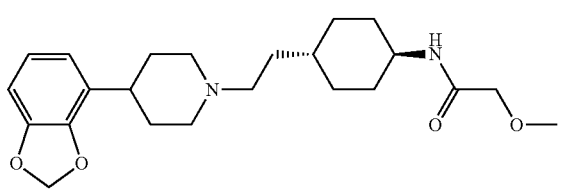 [SMILES: COCC(=O)N[C@H]1CC[C@H](CCN2CCC(c3cccc4c3OCO4)CC2)CC1]

The title compound, white solid (13.9 mg, 43.2%), MS (ISP) m/z=403.3 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and 2-methoxyacetic acid

Example 14

Trans-N-{4-[2-(4-Benzo[1,3]dioxol-4-yl-piperidin-1-yl)-ethyl]-cyclohexyl}-4-cyano-benzamide

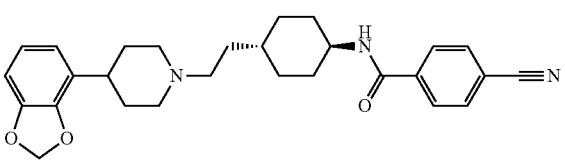 [SMILES: N#Cc1ccc(C(=O)N[C@H]2CC[C@H](CCN3CCC(c4cccc5c4OCO5)CC3)CC2)cc1]

The title compound, white solid (24.9 mg, 67.7%), MS (ISP) m/z=460.4 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and 4-cyanobenzoic acid.

Example 15

Trans-N-{4-[2-(4-Benzo[1,3]dioxol-4-yl-piperidin-1-yl)-ethyl]-cyclohexyl}-6-methyl-nicotinamide

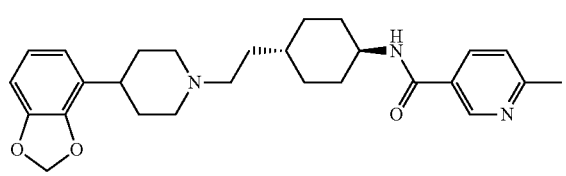 [SMILES: Cc1ccc(C(=O)N[C@H]2CC[C@H](CCN3CCC(c4cccc5c4OCO5)CC3)CC2)cn1]

The title compound, white solid (22.6 mg, 62.8%), MS (ISP) m/z=450.0 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (29.4 mg, 0.080 mmol) and 6-methylnicotinic acid

Example 16

Trans-N-{4-[2-(4-Benzo[1,3]dioxol-4-yl-piperidin-1-yl)-ethyl]-cyclohexyl}-2-(R)-tetrahydro-furan-2-yl-acetamide

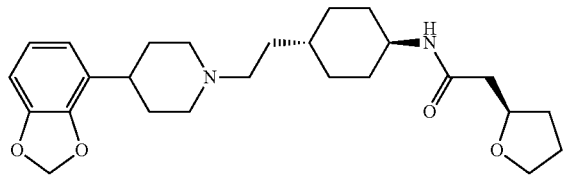 [SMILES: O=C(C[C@H]1CCCO1)N[C@H]1CC[C@H](CCN2CCC(c3cccc4c3OCO4)CC2)CC1]

The title compound, off-white solid (34 mg, 62%), MS (ISP) m/z=443.5 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (50 mg, 0.124 mmol) and (R)-2-(tetrahydrofuran-2-yl)acetic acid

Example 17

Trans-N-{4-[2-(4-Benzo[1,3]dioxol-4-yl-piperidin-1-yl)-ethyl]-cyclohexyl}-2-(S)-tetrahydro-furan-2-yl-acetamide

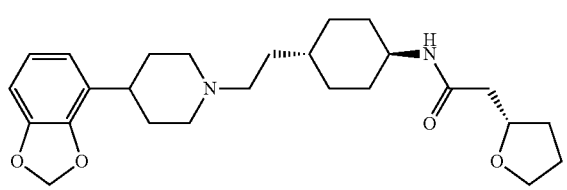

The title compound, off-white solid (40 mg, 72.9%), MS (ISP) m/z=443.5 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (50 mg, 0.124 mmol) and (S)-2-(tetrahydrofuran-2-yl)acetic acid Example 18

Trans-{4-[2-(4-Benzo[1,3]dioxol-4-yl-piperidin-1-yl)-ethyl]-cyclohexyl}-carbamic acid methyl ester

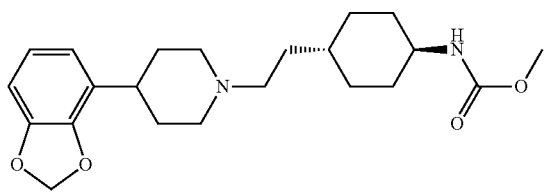 [SMILES: COC(=O)N[C@H]1CC[C@H](CCN2CCC(c3cccc4c3OCO4)CC2)CC1]

The title compound was prepared from Trans-4-[2-(4-Benzo[1,3]dioxol-4-yl-piperidin-1-yl)-ethyl]-cyclohexylamine hydrochloride (intermediate A) (25 mg, 0.068 mmol) and triethylamine (20.6 mg, 28.4 µl, 204 µmol) in dichloromethane (1 mL). Methyl carbonochloridate (7.06 mg, 5.78 µl, 0.075 µmol) was added to the mixture stirring at 0° C. The ice bath was removed and the reaction mixture was stirred for 1 hour at room temp. The reaction was diluted with dichloromethane and quenched with sat NaHCO3 (4 mL). The aqueous layer was extracted with DCM (1×5 mL). The organic layers were dried over MgSO$_4$ and concentrated in vacuo. The crude material was purified by flash chromatography (silica gel, 10 g, 0% to 15% MeOH in dichloromethane) to yield the title compound as a white solid (11 mg, 41.6%), MS (ISP) m/z=389.1 [(M+H)$^+$].

Example 19

Trans-N-{4-[2-(4-Benzo[1,3]dioxol-4-yl-piperidin-1-yl)-ethyl]-cyclohexyl}-2-(3-methyl-isoxazol-5-yl)-acetamide

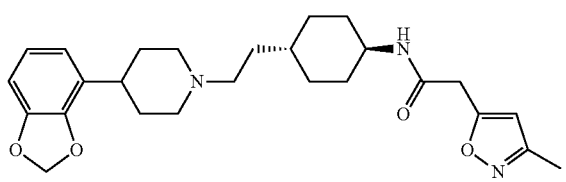 [SMILES: Cc1cc(CC(=O)N[C@H]2CC[C@H](CCN3CCC(c4cccc5c4OCO5)CC3)CC2)on1]

The title compound, light yellow solid (23 mg, 72.4%), MS (ISP) m/z=454.4 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.07 mmol) and 2-(3-methylisoxazol-5-yl)acetic acid.

Example 20

Trans-N-{-4-[2-(4-Benzo[1,3]dioxol-4-yl-piperidin-1-yl)-ethyl]-cyclohexyl}-2-cyano-acetamide

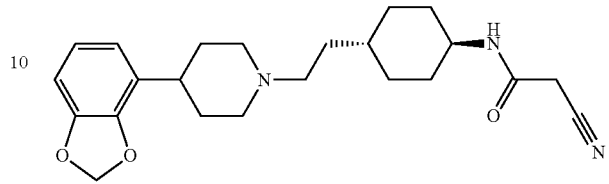

The title compound, light yellow solid (14.9 mg, 53.5%), MS (ISP) m/z=398.1 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.07 mmol) and 2-cyanoacetic acid.

Example 21

Trans-N-{4-[2-(4-Benzo[1,3]dioxol-4-yl-piperidin-1-yl)-ethyl]-cyclohexyl}-2-(1-hydroxy-cyclohexyl)-acetamide

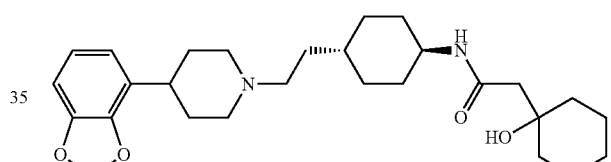

The title compound, light yellow solid (21.3 mg, 64.7%), MS (ISP) m/z=471.5[(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.07 mmol) and 2-(1-hydroxycyclohexyl)acetic acid Example 22

Trans-N-{4-[2-(4-Benzo[1,3]dioxol-4-yl-piperidin-1-yl)-ethyl]-cyclohexyl}-2-(tetrahydro-pyran-2-yl)-acetamide

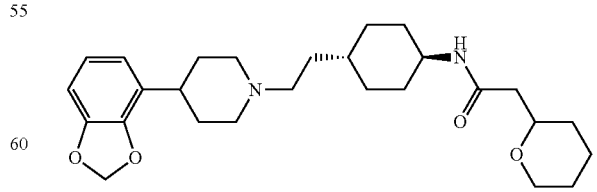

The title compound, light yellow solid (17.1 mg, 53.5%), MS (ISP)m/z=457.5[(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.07 mmol) and 2-(tetrahydro-2H-pyran-2-yl)acetic acid Example 23

Trans-N-{4-[2-(4-Benzo[1,3]dioxol-4-yl-piperidin-1-yl)-ethyl]-cyclohexyl}-isobutyramide

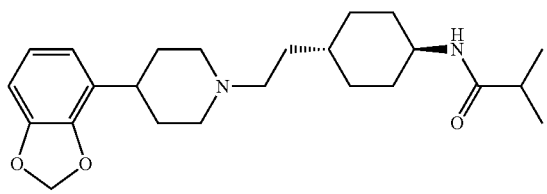

The title compound, light yellow solid (13.9 mg, 49.6%), MS (ISP) m/z=401.5[(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.07 mmol) and isobutyric acid.

Example 24

Trans-N-{4-[2-(4-Benzo[1,3]dioxol-4-yl-piperidin-1-yl)-ethyl]-cyclohexyl}-3-methyl-butyramide

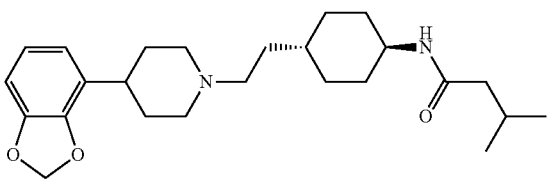 [SMILES: CC(C)CC(=O)N[C@H]1CC[C@H](CCN2CCC(c3cccc4c3OCO4)CC2)CC1]

The title compound, light yellow solid (9.1 mg, 31.4%), MS (ISP) m/z=415.5[(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.07 mmol) and 3-methylbutanoic acid Example 25

Trans-N-{4-[2-(4-Benzo[1,3]dioxol-4-yl-piperidin-1-yl)-ethyl]-cyclohexyl}-butyramide

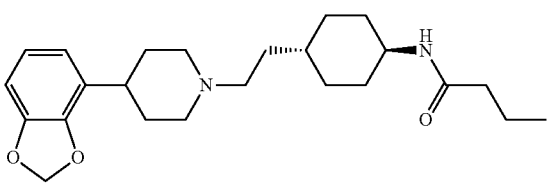

The title compound, light yellow solid (12.9 mg, 46%), MS (ISP) m/z=401.4[(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.07 mmol) and butyric acid Example 26

Trans-2,2-Difluoro-cyclopropanecarboxylic acid {4-[2-(4-benzo[1,3]dioxol-4-yl-piperidin-1-yl)-ethyl]-cyclohexyl}-amide

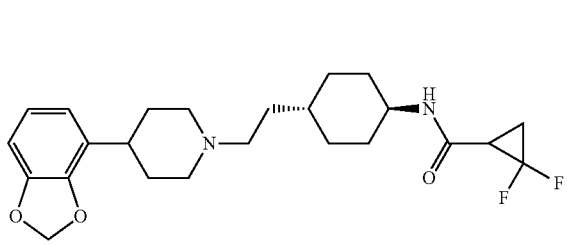 [SMILES: O=C(N[C@H]1CC[C@H](CCN2CCC(c3cccc4c3OCO4)CC2)CC1)C1CC1(F)F]

The title compound, white solid (9.7 mg, 31.9%), MS (ISP) m/z=435.4 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and 2,2-difluorocyclopropanecarboxylic acid Example 27

Trans-N-{4-[2-(4-Benzo[1,3]dioxol-4-yl-piperidin-1-yl)-ethyl]-cyclohexyl}-3-methoxy-butyramide

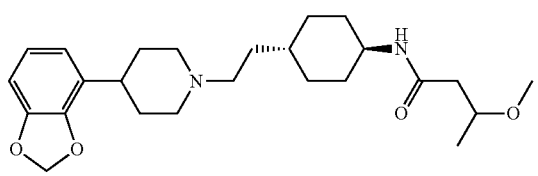 [SMILES: COC(C)CC(=O)N[C@H]1CC[C@H](CCN2CCC(c3cccc4c3OCO4)CC2)CC1]

The title compound, white solid (13.9 mg, 46.1%), MS (ISP) m/z=431.5 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and 3-methoxybutanoic acid Example 28

3-Chloro-cyclobutanecarboxylic acid trans-{4-[2-(4-benzo[1,3]dioxol-4-yl-piperidin-1-yl)-ethyl]-cyclohexyl}-amide

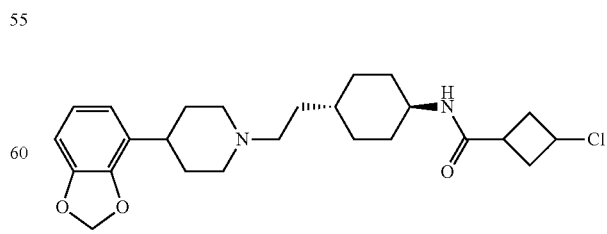

The title compound, white solid (15 mg, 51.4%), MS (ISP) m/z=447.4 [(M+H)⁺], was prepared in accordance with the general method of example 1 from Trans-4-[2-(4-Benzo[1,3]

dioxol-4-yl-piperidin-1-yl)-ethyl]-cyclohexylamine hydrochloride (intermediate A) ((25 mg, 0.062 mmol) and 3-chlorocyclobutanecarboxylic acid

Example 29

Trans-N-{4-[2-(4-Benzo[1,3]dioxol-4-yl-piperidin-1-yl)-ethyl]cyclohexyl}-2-oxetan-3-yl-acetamide

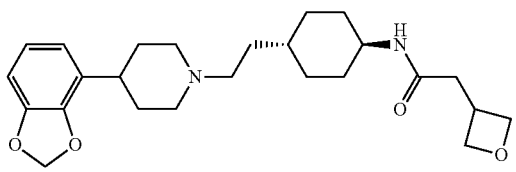 [SMILES: O=C(CC1COC1)N[C@H]1CC[C@H](CCN2CCC(c3cccc4c3OCO4)CC2)CC1]

The title compound, white solid (22.9 mg, 76.3%), MS (ISP) m/z=429.5 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and methyl 2-(oxetan-3-yl)acetate.

Example 30

Trans-N-{4-[2-(4-Benzo[1,3]dioxol-4-yl-piperidin-1-yl)-ethyl]-cyclohexyl}-2-((1R,3R)-3-methoxy-cyclopentyl)-acetamide

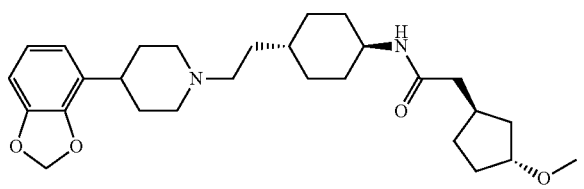 [SMILES: CO[C@@H]1CC[C@@H](CC(=O)N[C@H]2CC[C@H](CCN3CCC(c4cccc5c4OCO5)CC3)CC2)C1]

The title compound, white solid (22.2 mg, 77.4%), MS (ISP) m/z=471.5 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and methyl 2-((1R,3R)-3-methoxycyclopentyl)acetate.

Example 31

Trans-N-{4-[2-(4-Benzo[1,3]dioxol-4-yl-piperidin-1-yl)-ethyl]-cyclohexyl}-2-(4-hydroxy-tetrahydro-pyran-4-yl)-acetamide

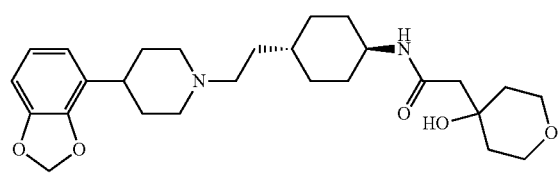 [SMILES: O=C(CC1(O)CCOCC1)N[C@H]1CC[C@H](CCN2CCC(c3cccc4c3OCO4)CC2)CC1]

The title compound, white solid (15.7 mg, 48.8%), MS (ISP) m/z=473.5 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.0 mg, 0.0681 mmol) and (4-Hydroxy-tetrahydro-pyran-4-yl)-acetic acid.

Example 32

Trans-N-{4-[2-(4-Benzo[1,3]dioxol-4-yl-piperidin-1-yl)-ethyl]-cyclohexyl}-2-hydroxy-2-methyl-propionamide

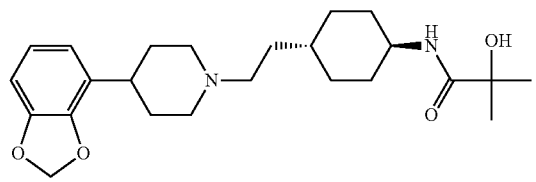 [SMILES: CC(C)(O)C(=O)N[C@H]1CC[C@H](CCN2CCC(c3cccc4c3OCO4)CC2)CC1]

The title compound, white solid (12.3 mg, 42.2%), MS (ISP) m/z=417.5 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and 2-hydroxy-2-methylpropanoic acid

Example 33

Trans-(S)—N-{4-[2-(4-Benzo[1,3]dioxol-4-yl-piperidin-1-yl)-ethyl]-cyclohexyl}-2-methoxy-propionamide

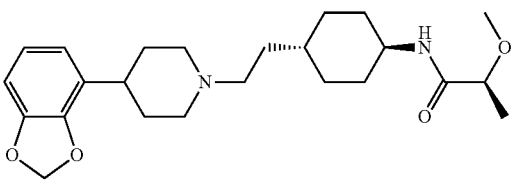 [SMILES: CO[C@@H](C)C(=O)N[C@H]1CC[C@H](CCN2CCC(c3cccc4c3OCO4)CC2)CC1]

The title compound, white solid (14.2 mg, 48.7%), MS (ISP) m/z=417.5 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and (S)-2-methoxypropanoic acid

Example 34

Trans-(R)—N-{4-[2-(4-Benzo[1,3]dioxol-4-yl-piperidin-1-yl)-ethyl]-cyclohexyl}-2-methoxy-propionamide

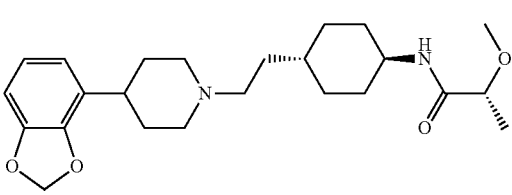 [SMILES: CO[C@H](C)C(=O)N[C@H]1CC[C@H](CCN2CCC(c3cccc4c3OCO4)CC2)CC1]

The title compound, white solid (19 mg, 65.2%), MS (ISP) m/z=417.5 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and (R)-2-methoxypropanoic acid.

Example 35

Trans-N-{4-[2-(4-Benzo[1,3]dioxol-4-yl-piperidin-1-yl)-ethyl]-cyclohexyl}-3-hydroxy-3-methyl-butyramide

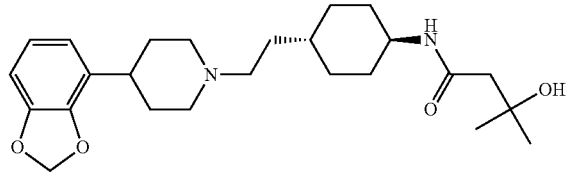 [SMILES: CC(C)(O)CC(=O)N[C@H]1CC[C@H](CCN2CCC(c3cccc4c3OCO4)CC2)CC1]

The title compound, white solid (18.7 mg, 62%), MS (ISP) m/z=431.4 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and 3-hydroxy-3-methylbutanoic acid Example 36

Trans-N-{4-[2-(4-Benzo[1,3]dioxol-4-yl-piperidin-1-yl)-ethyl]-cyclohexyl}-4-chloro-benzamide

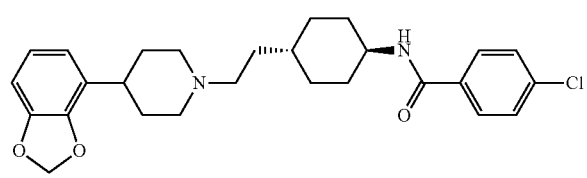 [SMILES: O=C(N[C@H]1CC[C@H](CCN2CCC(c3cccc4c3OCO4)CC2)CC1)c1ccc(Cl)cc1]

The title compound, white solid (22 mg, 74.9%), MS (ISP) m/z=469.3 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (24 mg, 0.0595 mmol) and 4-chlorobenzoic acid.

Example 37

Trans-N-{4-[2-(4-Benzo[1,3]dioxol-4-yl-piperidin-1-yl)-ethyl]-cyclohexyl}-4-fluoro-benzamide

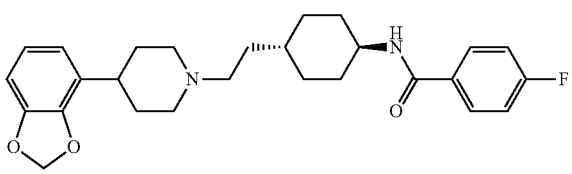 [SMILES: O=C(N[C@H]1CC[C@H](CCN2CCC(c3cccc4c3OCO4)CC2)CC1)c1ccc(F)cc1]

The title compound, white solid (17 mg, 60%), MS (ISP) m/z=453.2 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (24 mg, 0.0595 mmol) and 4-fluorobenzoic acid.

Example 38

Trans-(S)—N-{4-[2-(4-Benzo[1,3]dioxol-4-yl-piperidin-1-yl)-ethyl]-cyclohexyl}-3,3,3-trifluoro-2-hydroxy-propionamide

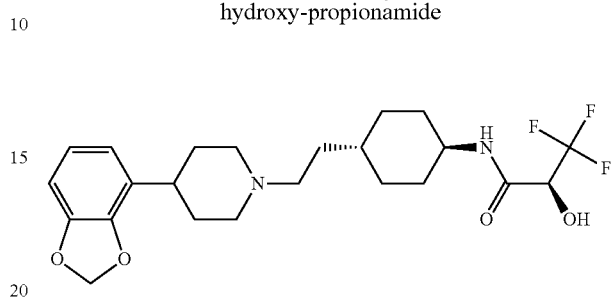

The title compound, white solid (14.7 mg, 47.3%), MS (ISP) m/z=457.2 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25 mg, 0.0681 mmol) and (S)-3,3,3-trifluoro-2-hydroxypropanoic acid.

Example 39

Trans-(R)—N-{4-[2-(4-Benzo[1,3]dioxol-4-yl-piperidin-1-yl)-ethyl]-cyclohexyl}-3,3,3-trifluoro-2-hydroxy-propionamide

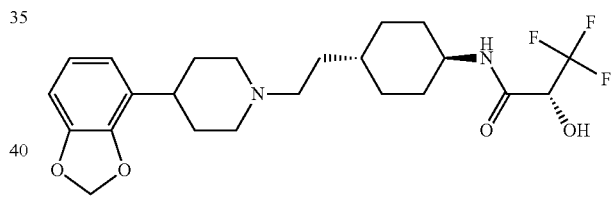

The title compound, white solid (17 mg, 54.7%), MS (ISP) m/z=457.2 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25 mg, 0.0681 mmol) and (R)-3,3,3-trifluoro-2-hydroxypropanoic acid Example 40

Trans-N-{4-[2-(4-Benzo[1,3]dioxol-4-yl-piperidin-1-yl)-ethyl]-cyclohexyl}-2-(S)-tetrahydro-pyran-2-yl-acetamide

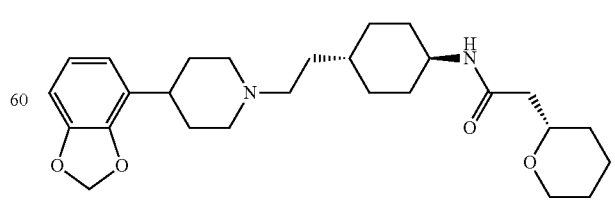

The title compound, off-white solid (21.5 mg, 67.3%), MS (ISP) m/z=457.3 [(M+H)+], was prepared in accordance with the general method of example 1 from Trans-4-(2-(4-Benzo

[1,3]dioxol-4-yl-piperidin-1-yl)-ethyl]-cyclohexylamine hydrochloride (intermediate A) (25.7 mg, 0.070 mmol) and (S)-2-(tetrahydro-2H-pyran-2-yl)acetic acid

Example 41

Trans-N-{4-[2-(4-Benzo[1,3]dioxol-4-yl-piperidin-1-yl)-ethyl]-cyclohexyl}-2-(R)-tetrahydro-pyran-2-yl-acetamide

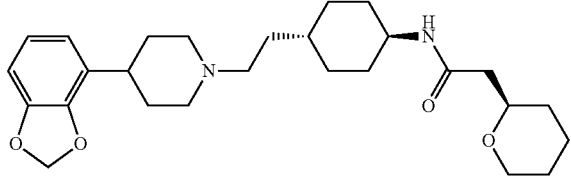 [SMILES: O=C(C[C@H]1CCCCO1)N[C@H]1CC[C@H](CCN2CCC(c3cccc4c3OCO4)CC2)CC1]

The title compound, white solid (20.9 mg, 65.4%), MS (ISP) m/z=457.3[(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and (R)-2-(tetrahydro-2H-pyran-2-yl)acetic acid

Example 42

Trans-N-{4-[2-(4-Benzo[1,3]dioxol-4-yl-piperidin-1-yl)-ethyl]-cyclohexyl}-2-(S)-tetrahydro-pyran-3-yl-acetamide

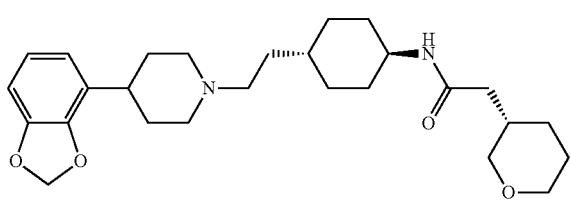 [SMILES: O=C(C[C@@H]1CCCOC1)N[C@H]1CC[C@H](CCN2CCC(c3cccc4c3OCO4)CC2)CC1]

The title compound, white solid (22.5 mg, 70.4%), MS (ISP) m/z=457.3 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and (S)-2-(tetrahydro-2H-pyran-3-yl)acetic acid

Example 43

Trans-N-{4-[2-(4-Benzo[1,3]dioxol-4-yl-piperidin-1-yl)-ethyl]-cyclohexyl}-2-(R)-tetrahydro-pyran-3-yl-acetamide

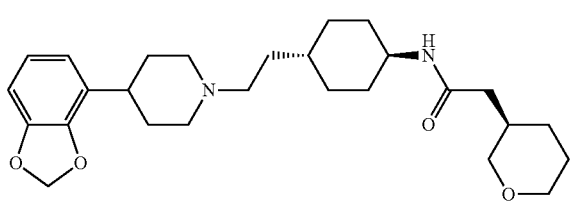 [SMILES: O=C(C[C@H]1CCCOC1)N[C@H]1CC[C@H](CCN2CCC(c3cccc4c3OCO4)CC2)CC1]

The title compound, white solid (20.9 mg, 65.4%), MS (ISP) m/z=457.3 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25.7 mg, 0.070 mmol) and (R)-2-(tetrahydro-2H-pyran-3-yl)acetic acid.

Example 44

Trans-N-{4-[2-(4-Benzo[1,3]dioxol-4-yl-piperidin-1-yl)-ethyl]-cyclohexyl}-3-ethoxy-propionamide

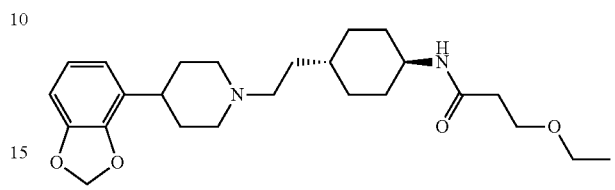

The title compound, white solid (23 mg, 68.2%), MS (ISP) m/z=431.3 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0744 mmol) and 3-ethoxypropanoic acid.

Example 45

Trans-N-{4-[2-(4-Benzo[1,3]dioxol-4-yl-piperidin-1-yl)-ethyl]-cyclohexyl}-2-(1-hydroxy-cyclobutyl)-acetamide

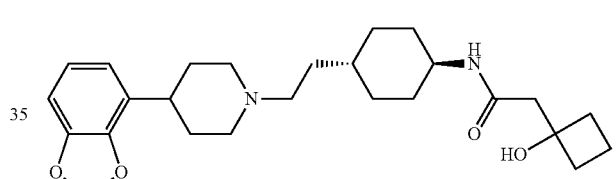

The title compound, white solid (20.5 mg, 68.2%), MS (ISP) m/z=443.3 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0744 mmol) and 2-(1-hydroxycyclobutyl)acetate acid prepared previously by saponification of the corresponding ethyl 2-(1-hydroxycyclobutyl)acetate using lithium hydroxide or another base in the presence of a solvent mixture such as tetrahydrofuran, water and methanol.

Example 46

Tetrahydro-furan-2-carboxylic acid-trans-{4-[2-(4-benzo[1,3]dioxol-4-yl-piperidin-1-yl)-ethyl]-cyclohexyl}-amide

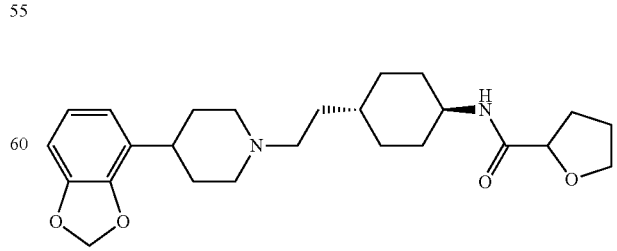

The title compound, white solid (17.6 mg, 60.3%), MS (ISP) m/z=429.2 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25 mg, 0.0681 mmol) and tetrahydrofuran-2-carboxylic acid Example 47

Tetrahydro-furan-3-carboxylic acid-trans-{4-[2-(4-benzo[1,3]dioxol-4-yl-piperidin-1-yl)-ethyl]-cyclohexyl}-amide

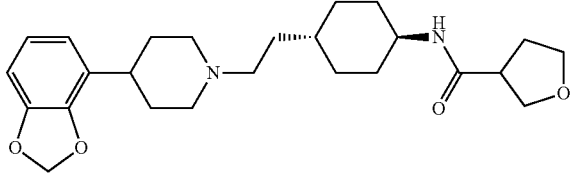 [SMILES: O=C(N[C@H]1CC[C@H](CCN2CCC(c3cccc4c3OCO4)CC2)CC1)C1CCOC1]

The title compound, white solid (17.6 mg, 60.3%), MS (ISP) m/z=429.2 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25 mg, 0.0681 mmol) and tetrahydrofuran-3-carboxylic acid.

Example 48

Tetrahydro-pyran-4-carboxylic acid-trans-{4-[2-(4-benzo[1,3]dioxol-4-yl-piperidin-1-yl)-ethyl]-cyclohexyl}-amide

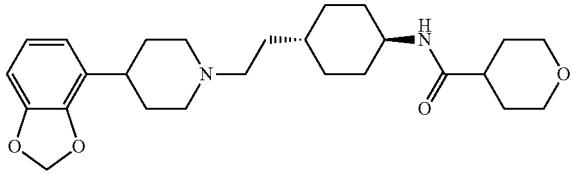 [SMILES: O=C(N[C@H]1CC[C@H](CCN2CCC(c3cccc4c3OCO4)CC2)CC1)C1CCOCC1]

The title compound, white solid (22.3 mg, 74%), MS (ISP) m/z=443.3 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25 mg, 0.0681 mmol) and tetrahydro-2H-pyran-4-carboxylic acid.

Example 49

1-Hydroxy-cyclopropanecarboxylic acid-trans-{4-[2-(4-benzo[1,3]dioxol-4-yl-piperidin-1-yl)-ethyl]-cyclohexyl}-amide

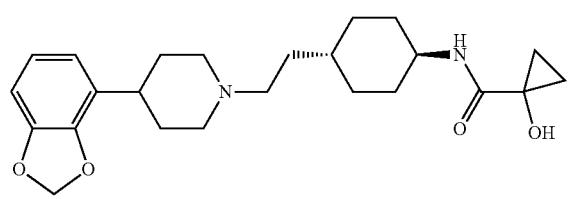 [SMILES: O=C(N[C@H]1CC[C@H](CCN2CCC(c3cccc4c3OCO4)CC2)CC1)C1(O)CC1]

The title compound, white solid (18.3 mg, 64.8%), MS (ISP) m/z=415.2 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25 mg, 0.0681 mmol) and 1-hydroxycyclopropanecarboxylic acid.

Example 50

Trifluoromethyl-cyclopropanecarboxylic acid-trans-N-{4-[2-(4-benzo[1,3]dioxol-4-yl-piperidin-1-yl)-ethyl]-cyclohexyl}-amide

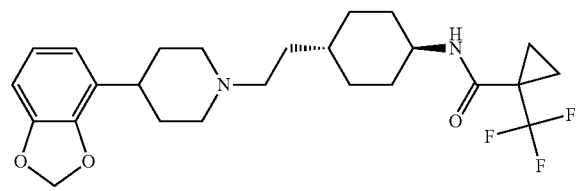 [SMILES: O=C(N[C@H]1CC[C@H](CCN2CCC(c3cccc4c3OCO4)CC2)CC1)C1(C(F)(F)F)CC1]

The title compound, white solid (10 mg, 31.5%), MS (ISP) m/z=467.2 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25 mg, 0.0681 mmol) and 1-(trifluoromethyl)cyclopropanecarboxylic acid.

Example 51

Trans-N-{4-[2-(4-Benzo[1,3]dioxol-4-yl-piperidin-1-yl)-ethyl]-cyclohexyl}-2-methyl-butyramide

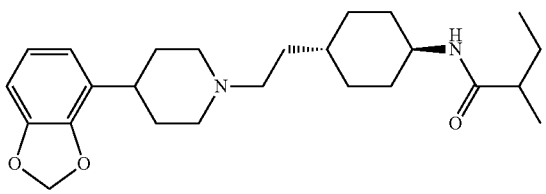 [SMILES: CCC(C)C(=O)N[C@H]1CC[C@H](CCN2CCC(c3cccc4c3OCO4)CC2)CC1]

The title compound, white solid (17.7 mg, 62.7%), MS (ISP) m/z=415.3 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (25 mg, 0.0681 mmol) and 2-methylbutanoic acid.

Example 52

1,1-Dioxo-tetrahydro-thiophene-3-carboxylic acid-trans-{4-[2-(4-benzo[1,3]dioxol-4-yl-piperidin-1-yl)-ethyl]-cyclohexyl}-amide

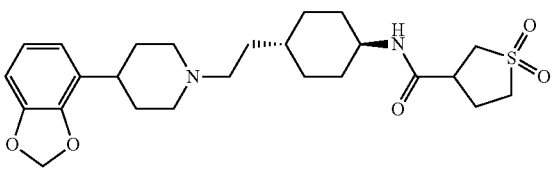 [SMILES: O=C(N[C@H]1CC[C@H](CCN2CCC(c3cccc4c3OCO4)CC2)CC1)C1CCS(=O)(=O)C1]

The title compound, white solid (21.1 mg, 54.1%), MS (ISP) m/z=477.2 [(M+H)+], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and 1,1-Dioxo-tetrahydro-thiophene-3-carboxylic acid.

Example 53

Trans-N-{4-[2-(4-Benzo[1,3]dioxol-4-yl-piperidin-1-yl)-ethyl]-cyclohexyl}-2-(tetrahydro-pyran-4-yl)-acetamide

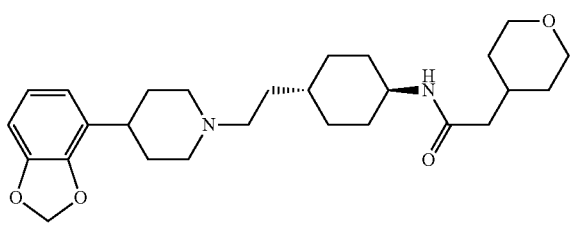 [SMILES: O=C(CC1CCOCC1)N[C@H]1CC[C@H](CCN2CCC(c3cccc4c3OCO4)CC2)CC1]

The title compound, white solid (29.3 mg, 78.5%), MS (ISP) m/z=457.3 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and 2-(tetrahydro-2H-pyran-4-yl)acetic acid.

Example 54

Cyclobutanecarboxylic acid-trans-{4-[2-(4-benzo[1,3]dioxol-4-yl-piperidin-1-yl)-ethyl]-cyclohexyl}-amide

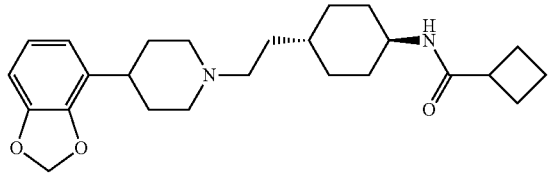 [SMILES: O=C(N[C@H]1CC[C@H](CCN2CCC(c3cccc4c3OCO4)CC2)CC1)C1CCC1]

The title compound, white solid (26.6 mg, 78.9%), MS (ISP) m/z=413.3 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and cyclobutanecarboxylic acid.

Example 55

Trans-N-{4-[2-(4-Benzo[1,3]dioxol-4-yl-piperidin-1-yl)-ethyl]cyclohexyl}-2-methanesulfonyl-acetamide

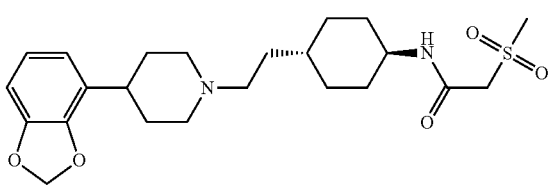 [SMILES: CS(=O)(=O)CC(=O)N[C@H]1CC[C@H](CCN2CCC(c3cccc4c3OCO4)CC2)CC1]

The title compound, white solid (25.3 mg, 68.7%), MS (ISP) m/z=451.1 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and 2-(methylsulfonyl)acetic acid.

Example 56

Trans-N-{-4-[2-(4-Benzo[1,3]dioxol-4-yl-piperidin-1-yl)-ethyl]-cyclohexyl}-4-morpholin-4-yl-benzamide

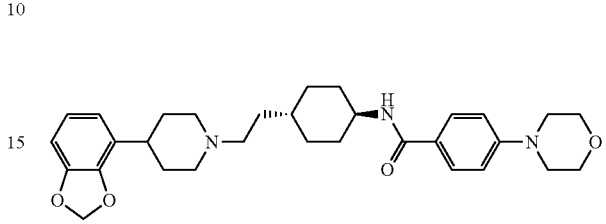

The title compound, white solid (31.1 mg, 73.2%), MS (ISP) m/z=520.3 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and 4-morpholinobenzoic acid.

Example 57

Quinoline-4-carboxylic acid-trans-N-{4-[2-(4-benzo[1,3]dioxol-4-yl-piperidin-1-yl)-ethyl]-cyclohexyl}-amide

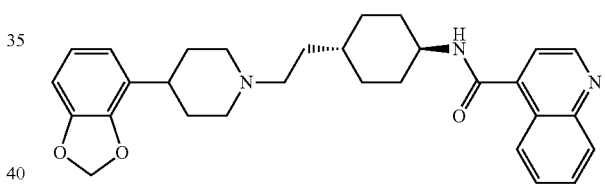

The title compound, white solid (29.6 mg, 74.6%), MS (ISP) m/z=486.3 [(M+H)⁺], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and quinoline-4-carboxylic acid.

Example 58

2,3-Dihydro-benzo[1,4]dioxine-6-carboxylic acid-trans-N-{4-[2-(4-benzo[1,3]dioxol-4-yl-piperidin-1-yl)-ethyl]-cyclohexyl}-amide

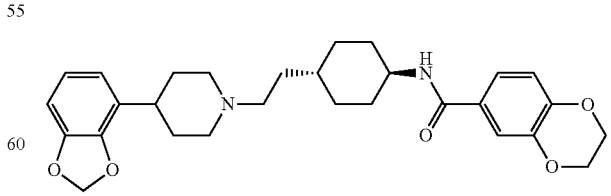

The title compound, white solid (28 mg, 69.5%), MS (ISP) m/z=493.3 [(M+H)⁺], was prepared in accordance with the general method of example 1 from Trans-4-[2-(4-Benzo[1,3]dioxol-4-yl-piperidin-1-yl)-ethyl]-cyclohexylamine hydro-

Example 59

2-Benzo[1,3]dioxol-5-yl-trans-N-{4-[2-(4-benzo[1,3]dioxol-4-yl-piperidin-1-yl)-ethyl]-cyclohexyl}-acetamide

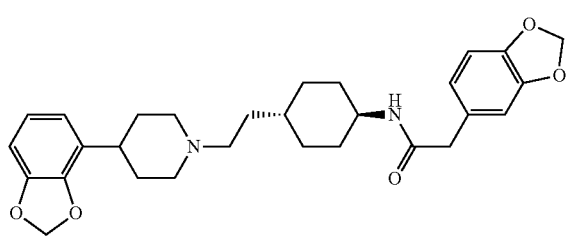 [SMILES: O=C(Cc1ccc2c(c1)OCO2)N[C@H]1CC[C@H](CCN2CCC(c3cccc4c3OCO4)CC2)CC1]

The title compound, white solid (21.8 mg, 54.1%), MS (ISP) m/z=493.3 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and 2-(benzo[d][1,3]dioxol-5-yl)acetic acid.

Example 60

Chroman-3-carboxylic acid-trans-N-{4-[2-(4-benzo[1,3]dioxol-4-yl-piperidin-1-yl)-ethyl]-cyclohexyl}-amide

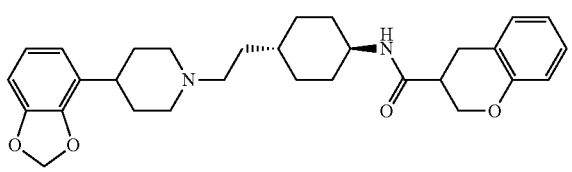 [SMILES: O=C(N[C@H]1CC[C@H](CCN2CCC(c3cccc4c3OCO4)CC2)CC1)C1COc2ccccc2C1]

The title compound, white solid (28.5 mg, 71%), MS (ISP) m/z=491.4 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and chroman-3-carboxylic acid.

Example 61

1-Methyl-piperidine-4-carboxylic acid-trans-N-{4-[2-(4-benzo[1,3]dioxol-4-yl-piperidin-1-yl)-ethyl]-cyclohexyl}-amide

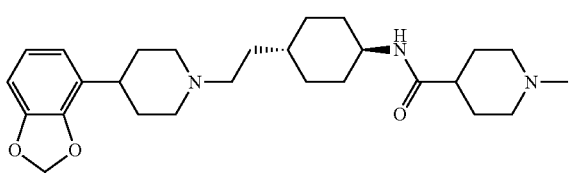

The title compound, white solid (26.9 mg, 69.5%), MS (ISP) m/z=456.3 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (31.2 mg, 0.085 mmol) and 1-methylpiperidine-4-carboxylic acid.

Example 62

3-Methyl-oxetane-3-carboxylic acid-trans-N-{4-[2-(4-benzo[1,3]dioxol-4-yl-piperidin-1-yl)-ethyl]-cyclohexyl}-amide

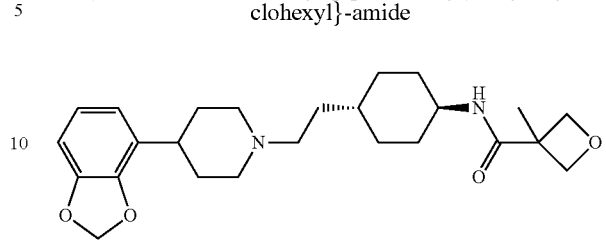

The title compound, white solid (13.6 mg, 37.3%), MS (ISP) m/z=429.2 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (31.2 mg, 0.085 mmol) and 3-methyl-oxetane-3-carboxylic acid.

Example 63

Trans-N-{4-[2-(4-Benzo[1,3]dioxol-4-yl-piperidin-1-yl)-ethyl]-cyclohexyl}-2-(4-methoxy-cyclohexyl)-acetamide

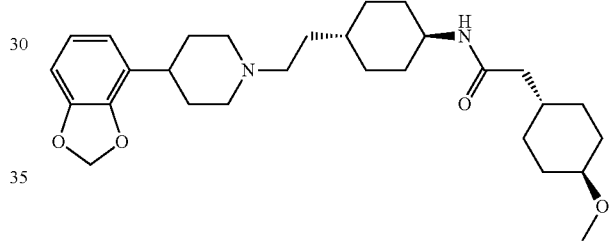

The title compound, white solid (30.8 mg, 77.7%), MS (ISP) m/z=485.4 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (31.2 mg, 0.085 mmol) and trans-(4-methoxycyclohexyl)acetic acid synthesized as described in W2009/013212 p. 73.

Example 64

(R)-trans-N-{4-[2-(4-Benzo[1,3]dioxol-4-yl-piperidin-1-yl)-ethyl]-cyclohexyl}-2-hydroxy-propionamide

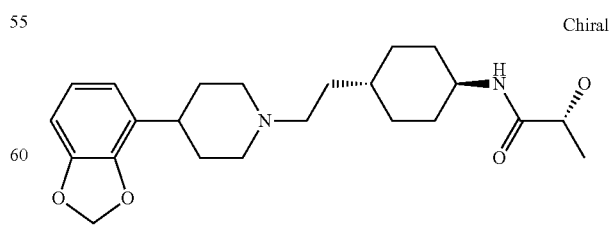

The title compound, white solid (17.7 mg, 53.8%), MS (ISP) m/z=403.3 [(M+H)$^+$], was prepared in accordance with the general method of example 1 from Trans-4-[2-(4-Benzo

[1,3]dioxol-4-yl-piperidin-1-yl)-ethyl]-cyclohexylamine hydrochloride (intermediate A) (30 mg, 0.0818 mmol) and (R)-2-hydroxypropanoic acid.

Example 65

Trans-N-{4-[2-(4-Benzo[1,3]dioxol-4-yl-piperidin-1-yl)-ethyl]-cyclohexyl}-2-hydroxy-acetamide

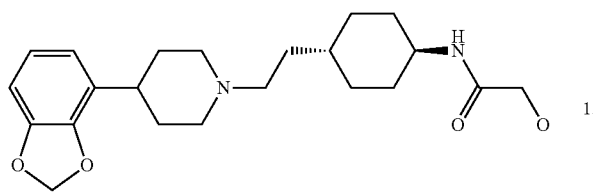

The title compound, white solid (14.9 mg, 46.9%), MS (ISP) m/z=389.1 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and 2-hydroxyacetic acid.

Example 66

1-Hydroxy-cyclohexanecarboxylic acid-trans-N-{4-[2-(4-benzo[1,3]dioxol-4-yl-piperidin-1-yl)-ethyl]-cyclohexyl}-amide

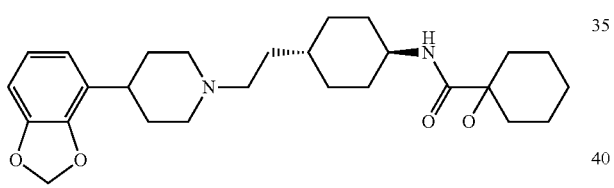 [SMILES: CN1CCC(C(=O)N[C@H]2CC[C@H](CCN3CCC(c4cccc5c4OCO5)CC3)CC2)CC1]

The title compound, white solid (14.9 mg, 39.9%), MS (ISP) m/z=457.3 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and 1-hydroxycyclohexanecarboxylic acid.

Example 67

1-Methoxy-cyclohexanecarboxylic acid-trans-N-{4-[2-(4-benzo[1,3]dioxol-4-yl-piperidin-1-yl)-ethyl]-cyclohexyl}-amide

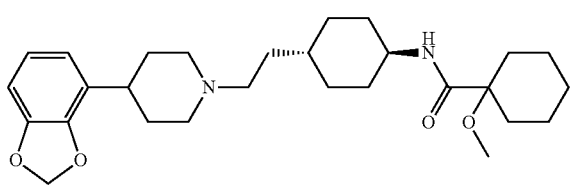 [SMILES: COC1(C(=O)N[C@H]2CC[C@H](CCN3CCC(c4cccc5c4OCO5)CC3)CC2)CCCCC1]

The title compound, white solid (22.2 mg, 57.7%), MS (ISP) m/z=471.3 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and 1-Methoxycyclohexane-1-carboxylic acid.

Example 68

Trans-N-{4-[2-(4-Benzo[1,3]dioxol-4-yl-piperidin-1-yl)-ethyl]-cyclohexyl}-2-(4-methylpiperazin-1-yl)-acetamide

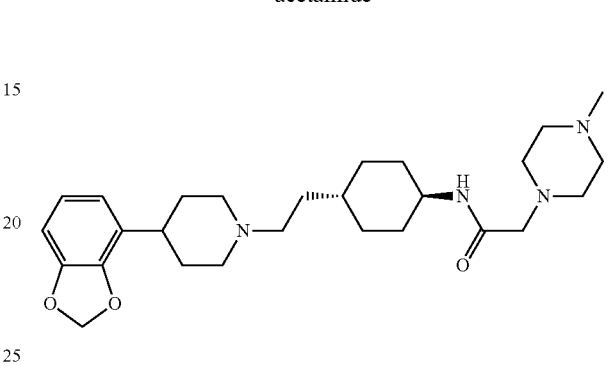

The title compound, white solid (13.5 mg, 35.1%), MS (ISP) m/z=471.3 [(M+H)$^+$], was prepared in accordance with the general method of example 1 from Trans-4-[2-(4-Benzo[1,3]dioxol-4-yl-piperidin-1-yl)-ethyl]-cyclohexylamine hydrochloride (intermediate A) (30 mg, 0.0818 mmol) and 2-(4-methylpiperazin-1-yl)acetic acid.

Example 69

Trans-N-{4-[2-(4-Benzo[1,3]dioxol-4-yl-piperidin-1-yl)-ethyl]-cyclohexyl}-methanesulfonamide

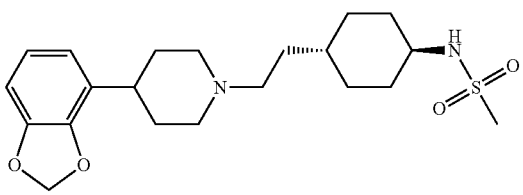 [SMILES: CS(=O)(=O)N[C@H]1CC[C@H](CCN2CCC(c3cccc4c3OCO4)CC2)CC1]

To a stirred mixture of Trans-4-[2-(4-Benzo[1,3]dioxol-4-yl-piperidin-1-yl)-ethyl]-cyclohexylamine hydrochloride (intermediate A) (30 mg, 0.0818 mmol, Eq: 1.00) in dichloromethane (500 µl) was added at room temperature N,N-diisopropylethylamine (31.6 mg, 42.7 µl, 245 µmol, Eq: 3) and methanesulfonyl chloride (14.1 mg, 123 µmol). The mixture was allowed to stir at room temperature over night. The crude reaction diluted with 5 mL sat NaHCO$_3$ and extracted with DCM (2×10 mL). The organic layers were dried over MgSO$_4$ and concentrated in vacuo. The crude material was purified by flash chromatography (silica gel, 10 g, 0% to 10% MeOH in DCM) to yield the title compound as an white solid (16.2 mg, 48.5%), MS (ISP) m/z=409.3 [(M+H)$^+$].

Example 70

Trans-N-{4-[2-(4-Benzo[1,3]dioxol-4-yl-piperidin-1-yl)-ethyl]cyclohexyl}-benzenesulfonamide

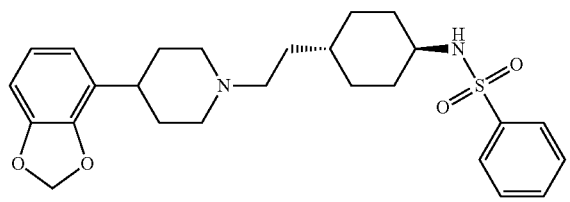 [SMILES: O=S(=O)(N[C@H]1CC[C@H](CCN2CCC(c3cccc4c3OCO4)CC2)CC1)c1ccccc1]

The title compound, white solid (25.7 mg, 66.8%), MS (ISP) m/z=471.3 [(M+H)+], was prepared in accordance with the general method of example 69 from Trans-4-[2-(4-Benzo[1,3]dioxol-4-yl-piperidin-1-yl)-ethyl]-cyclohexylamine hydrochloride (intermediate A) (30 mg, 0.0818 mmol) and benzenesulfonyl chloride.

Example 71

N-trans-{4-[2-(4-Benzo[1,3]dioxol-4-yl-piperidin-1-yl)-ethyl]-cyclohexyl}-4-fluoro-benzenesulfonamide

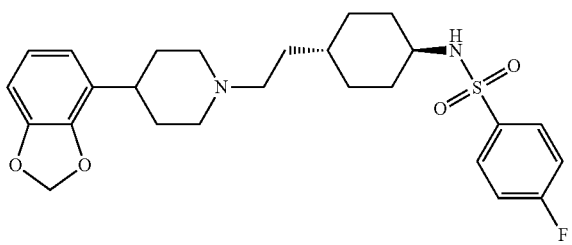 [SMILES: O=S(=O)(N[C@H]1CC[C@H](CCN2CCC(c3cccc4c3OCO4)CC2)CC1)c1ccc(F)cc1]

The title compound, white solid (24.2 mg, 60.5%), MS (ISP) m/z=489.3 [(M+H)+], was prepared in accordance with the general method of example 69 from Trans-4-[2-(4-Benzo[1,3]dioxol-4-yl-piperidin-1-yl)-ethyl]-cyclohexylamine hydrochloride (intermediate A) (30 mg, 0.0818 mmol) and 4-fluorobenzene-1-sulfonyl chloride.

Example 72

1-Methyl-1H-imidazole-4-sulfonic acid-trans-N-{4-[2-(4-benzo[1,3]dioxol-4-yl-piperidin-1-yl)-ethyl]-cyclohexyl}-amide

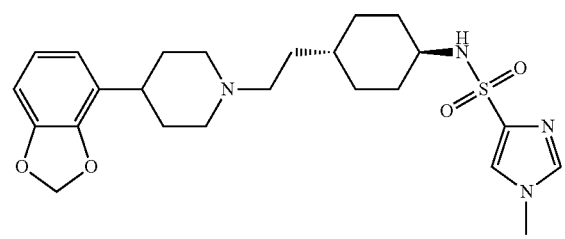 [SMILES: Cn1cnc(S(=O)(=O)N[C@H]2CC[C@H](CCN3CCC(c4cccc5c4OCO5)CC3)CC2)c1]

The title compound, white solid (19.5 mg, 45.3%), MS (ISP) m/z=475.1 [(M+H)+], was prepared in accordance with the general method of example 69 from Trans-4-[2-(4-Benzo[1,3]dioxol-4-yl-piperidin-1-yl)-ethyl]-cyclohexylamine hydrochloride (intermediate A) (30 mg, 90.8 mmol) and 1-methyl-1H-imidazole-4-sulfonyl chloride.

Example 73

Trans-N-{4-[2-(4-Benzo[1,3]dioxol-4-yl-piperidin-1-yl)-ethyl]-cyclohexyl}-2,2,2-trifluoro-acetamide

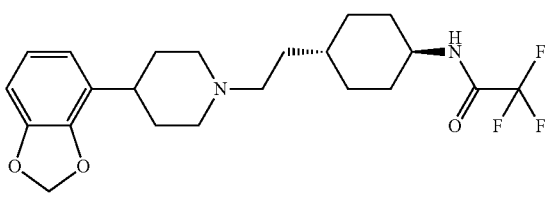 [SMILES: O=C(N[C@H]1CC[C@H](CCN2CCC(c3cccc4c3OCO4)CC2)CC1)C(F)(F)F]

To a stirred mixture of Trans-4-[2-(4-Benzo[1,3]dioxol-4-yl-piperidin-1-yl)-ethyl]-cyclohexylamine hydrochloride (intermediate A) (30 mg, 0.0818 mmol, Eq: 1.00) in dichloromethane (1000 µl) at 0° C. was added Triethylamine (16.5 mg, 22.8 µl, 164 µmol, Eq: 2) and 2,2,2-trifluoroacetic anhydride (85.9 mg, 56.8 µl, 409 µmol, Eq: 5). The mixture was allowed to stir for 1 hour at 0° C. The reaction mixture was quenched with 10 mL sat NaHCO3 and extracted with DCM (3×15 mL). The organic layers were dried over MgSO4 and concentrated in vacuo. The crude material was purified by flash chromatography (silica gel, 10 g, 0% to 10% MeOH in DCM) to yield the title compound as an white solid (21.6 mg, 61.9%), MS (ISP) m/z=427.3 [(M+H)+].

Example 74

2,3-Dihydro-indole-1-carboxylic acid N-trans-{4-[2-(4-benzo[1,3]dioxol-4-yl-piperidin-1-yl)-ethyl]-cyclohexyl}-amide

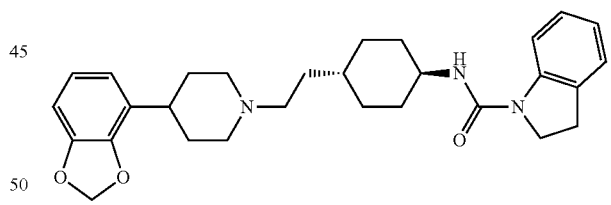

To a stirred mixture of Trans-4-[2-(4-Benzo[1,3]dioxol-4-yl-piperidin-1-yl)-ethyl]-cyclohexylamine hydrochloride (Intermediate A) (31.2 mg, 85 µmol, Eq: 1) in DCM (1 ml) at room temperature N,N-diisopropylethylamine (110 mg, 148 µl, 850 µmol, Eq: 10) and Triphosgene (27.7 mg, 93.5 µmol, Eq: 1.1) was added carefully and the solution stirred for 30 minutes at room temperature. Indoline (12.2 mg, 102 µmol, Eq: 1.2) was added and stirred for 30 minutes at room temperature. The reaction mixture was quenched with 10 mL sat NaHCO3 and extracted with DCM (3×15 mL). The organic layers were dried over MgSO4 and concentrated in vacuo. The crude material was purified by flash chromatography (silica gel, 10 g, 0% to 10% MeOH in DCM) to yield the title compound as an white solid (28.3 mg, 70%), MS (ISP) m/z=476.2 [(M+H)+].

Example 75

N-Trans-3-{4-[2-(4-Benzo[1,3]dioxol-4-yl-piperidin-1-yl)-ethyl]cyclohexyl}-1,1-dimethyl-urea

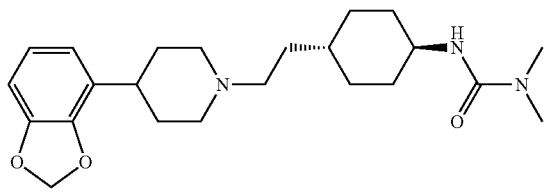 [SMILES: CN(C)C(=O)N[C@H]1CC[C@H](CCN2CCC(c3cccc4c3OCO4)CC2)CC1]

The title compound, white solid (19.8 mg, 58%), MS (ISP) m/z=402.3 [(M+H)$^+$], was prepared in accordance with the general method of example 74 from Trans-4-[2-(4-Benzo[1,3]dioxol-4-yl-piperidin-1-yl)-ethyl]-cyclohexylamine hydrochloride (intermediate A) (31.2 mg, 85 µmol) and dimethylamine hydrochloride.

Example 76

Trans-N-{4-[2-(4-Benzo[1,3]dioxol-4-yl-piperidin-1-yl)-ethyl]-cyclohexyl}-2-fluoro-acetamide

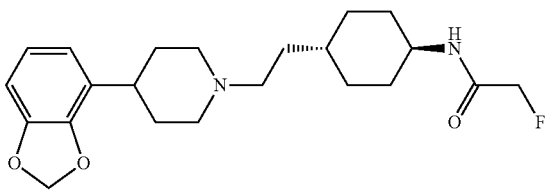 [SMILES: O=C(CF)N[C@H]1CC[C@H](CCN2CCC(c3cccc4c3OCO4)CC2)CC1]

A mixture of methyl 2-fluoroacetate (11.3 mg, 123 µmol, Eq: 1.5) and KOSiMe$_3$ (21 mg, 164 µmol, Eq: 2) in Dioxane (1 ml) was stirred at room temperature over night. Trans-4-[2-(4-Benzo[1,3]dioxol-4-yl-piperidin-1-yl)-ethyl]-cyclohexylamine hydrochloride (Intermediate A) (30 mg, 81.8 µmol), N,N-diisopropylethylamine (42.3 mg, 57.0 µl, 327 µmol, Eq: 4) and TBTU (39.4 mg, 123 µmol, Eq: 1.5) were added. Reaction mixture was stirred 4 h at room temperature. The reaction mixture was solved with sat NaHCO$_3$ (1×10 mL) and extracted with dichloromethane (2×20 mL). The organic layers were dried over MgSO$_4$ and concentrated in vacuo. The crude material was purified by flash chromatography (silica gel, 10 g, 0% to 20% MeOH in dichloromethane) to yield the title compound as an off-white solid (21.3 mg, 66.7%), MS (ISP) m/z=391.2 [(M+H)$^+$].

Example 77

N-trans-1-{4-[2-(4-Benzo[1,3]dioxol-4-yl-piperidin-1-yl)-ethyl]-cyclohexyl}-3-(4-chloro-phenyl)-urea

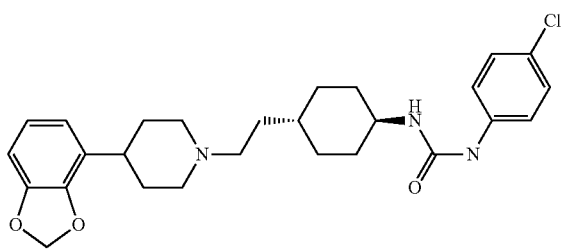 [SMILES: O=C(Nc1ccc(Cl)cc1)N[C@H]1CC[C@H](CCN2CCC(c3cccc4c3OCO4)CC2)CC1]

To a stirred mixture of Trans-4-[2-(4-Benzo[1,3]dioxol-4-yl-piperidin-1-yl)-ethyl]-cyclohexylamine (Intermediate A) (25 mg, 75.7 µmol) in Acetonitrile (800 µl) was added 1-chloro-4-isocyanatobenzene (12.8 mg, 83.2 µmol, Eq: 1.1. Reaction mixture was stirred at room temperature over night. The reaction mixture was solved with sat NaHCO$_3$ (1×10 mL) and extracted with dichloromethane (2×20 mL). The organic layers were dried over MgSO4 and concentrated in vacuo. The crude material was purified by flash chromatography (silica gel, 10 g, 0% to 20% MeOH in dichloromethane) to yield the title compound as an off-white solid (9.2 mg, 25.1%), MS (ISP) m/z=484.1 [(M+H)$^+$].

Example 78

Trans-N-{4-[2-(4-benzo[1,3]dioxol-4-yl-piperidin-1-yl)-ethyl]-cyclohexyl}-N,N-dimethyl-sulfamide

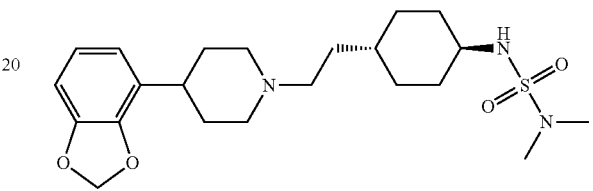

To a stirred mixture of Trans-4-[2-(4-Benzo[1,3]dioxol-4-yl-piperidin-1-yl)-ethyl]-cyclohexylamine hydrochloride (Intermediate A) (31.2 mg, 85 µmol) in acetonitrile (1 ml) was added dimethylsulfamoyl chloride (18.4 mg, 128 µmol, Eq: 1.5) and DABCO (33.4 mg, 298 µmol, Eq: 3.5). Reaction mixture was stirred at room temperature for 24 hours. The reaction mixture was solved with sat NaHCO$_3$ (1×10 mL). and extracted with dichloromethane (2×20 mL). The organic layers were dried over MgSO4 and concentrated in vacuo. The crude material was purified by flash chromatography (silica gel, 10 g, 0% to 20% MeOH in dichloromethane) to yield the title compound as an off-white solid (9.2 mg, 24.7%), MS (ISP) m/z=438.2 [(M+H)$^+$].

Example 79

Morpholine-4-sulfonic acid-Trans-N-{4-[2-(4-benzo[1,3]dioxol-4-yl-piperidin-1-yl)-ethyl]-cyclohexyl}-amide

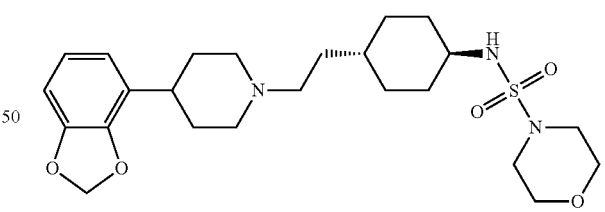

The title compound, white solid (5.4 mg, 13.2%), MS (ISP) m/z=480.2 [(M+H)$^+$], was prepared in accordance with the general method of example 78 from Trans-4-[2-(4-Benzo[1,3]dioxol-4-yl-piperidin-1-yl)-ethyl]-cyclohexylamine hydrochloride (intermediate A) (31.2 mg, 85 mmol) and morpholine-4-sulfonyl chloride.

Biochemical Assay

The ability of the compounds to bind to the 5-HT$_{2A}$, D$_3$ and D$_2$ receptors was determined using radioligand binding to cloned receptors selectively expressed in HEK-293 EBNA cells.

Membrane Preparation

HEK293 EBNA cells were transiently transfected with expression plasmids encoding for the human $D_2$ or $D_3$ or for the human 5-$HT_{2A}$ receptor, respectively. The cells were harvested 48 h post-transfection, washed three times with cold PBS and stored at $-80°$ C. prior to use. The pellet was suspended in cold 50 mM Tris-HCl buffer containing 10 mM EDTA (pH 7.4) and was homogenized with a Polytron (Kinematica AG, Basel, Switzerland) for 20-30 sec at 12.000 rpm. After centrifugation at 48.000×g for 30 min at 4° C., the pellet was resuspended in cold 10 mM Tris-HCl buffer containing 0.1 mM EDTA (pH 7.4), homogenized, and centrifuged as above. This pellet was further resuspended in a smaller volume of ice cold 10 mM Tris-HCl buffer containing 0.1 mM EDTA (pH 7.4) and homogenized with a Polytron for 20-30 sec at 12.000 rpm. The protein content of this homogenate was determined with the Bio-Rad (Bradford) Protein Assay (Biorad Laboratories GmbH, München, Germany) according to the instructions of the manufacturer using gamma globulin as the standard. This homogenate was stored at $-80°$ C. in aliquots and thawed immediately prior to use.

Radioligand Binding Assay

Aliquots of membrane preparations were thawed at RT, resuspended in assay buffer ($D_2$, $D_3$: 50 mM Tris-HCl, 120 mM NaCl, 5 mM $MgCl_2$, 1 mM EDTA, 5 mM KCl, 1.5 mM $CaCl_2$, pH=7.4; 5-$HT_{2A}$: 50 mM Tris-HCl, 10 mM $MgCl_2$, 1 mM EGTA, pH=7.4), homogenized with a Polytron for 20-30 sec at 12.000 rpm and adjusted to a final concentration of approximately 7.5 μg protein/well ($D_2$, $D_3$) and 15 μg protein/well (5-$HT_{2A}$), respectively.

The binding affinity (IQ of the compounds was determined using radioligand binding. Membranes were incubated in a total volume of 200 μl with a fixed concentration of radioligand (final concentration approximately 0.7 nM [$^3$H]-spiperone for $D_2$, 0.5 nM [$^3$H]-spiperone for $D_3$, and 1.1 nM [$^3$H]-ketanserin for 5-$HT_{2A}$) and ten concentrations of test compound in ranging between 10 μM-0.1 nM for 1 h at RT. At the end of the incubation, the reaction mixtures were filtered on to unifilter 96-well white microplates with bonded GF/C filters (Packard BioScience, Zürich, Switzerland; preincubated for 1 h in 0.1% polyethylenimine (PEI) in assay buffer) with a Filtermate 196 harvester (Packard BioScience) and washed 3 times with cold assay buffer. The nonspecific binding was determined with equally composed reaction mixtures in the presence of 10 μM unlabelled spiperone. Per well 45 μl of Microscint 40 (Perkin Elmer, Schwerzenbach, Switzerland) was added, plates for sealed, shaken for 20 min and counted for 3 min on a Topcount Microplate Scintillation Counter (Can berra Packard SA, Zürich, Switzerland) with quenching correction.

Data Calculation

The CPM value for each duplicate of a concentration of competing compound was averaged (y1), then the % specific binding was calculated according to the equation (((y1-nonspecific)/(total binding-non-specific))×100). Graphs were plotted with the % specific binding using XLfit, a curve fitting program that iteratively plots the data using Levenberg-Marquardt algorithm. The single site competition analysis equation used was y=A+((B-A)/(1+((x/C)D))), where y is the % specific binding, A is the minimum y, B is the maximum y, C is the $IC_{50}$, x is the log 10 of the concentration of the competing compound and D is the slope of the curve (the Hill Coefficient). From these curves the $IC_{50}$ (inhibition concentration at which 50% specific binding of the radioligand was displaced) and Hill coefficient were determined. The affinity constant (K) was calculated using the Cheng-Prusoff equation $K_i=IC_{50}/1+([L]/K_d)$, where [L] is the concentration of radioligand and $K_d$ is the dissociation constant of the radioligand at the receptor as determined by the saturation isotherm.

The compounds of the present invention are selective dual modulators of the 5-$HT_{2A}$ and $D_3$ receptors as is shown in table 1 below. Examples were tested in the above assay and found to have $K_i$ 5-$HT_{2A}$ values of about 0.1 nM to about 1 μM and $K_i$ $D_3$ values of about 0.1 nM to about 1 μM. Particular compounds of formula (I) were found to have $K_i$ 5-$HT_{2A}$ values of about 1 nM to about 100 nM and $K_i$ $D_3$ values of about 1 nM to about 200 nM. Most particular compounds of formula (I) were found to have $K_i$ 5-$HT_{2A}$ values of about 1 nM to about 20 nM and $K_i$ $D_3$ values of about 1 nM to about 20 nM.

Particular compounds of formula (I) were found to bind more selectively to 5-$HT_{2A}$ receptor than $D_2$ receptor by a factor of 5 or more, more particularly 10 or more, most particularly 25 or more. Particular compounds of formula (I) were found to bind more selectively to $D_3$ receptor than $D_2$ receptor by a factor of 5 or more, more particularly 10 or more, most particularly 50 or more.

TABLE 1

Binding affinities to HEK293 EBNA cells expressing human (h) receptors of representative examples.

| Ex | $D_3$ $K_i$ (nM) | 5$HT_{2A}$ $K_i$ (nM) | $D_2$ $K_i$ (nM) |
|---|---|---|---|
| 1 | 4.99 | 23.85 | 253.68 |
| 2 | 5.82 | 38.20 | 426.60 |
| 3 | 8.88 | 13.94 | 529.67 |
| 4 | 9.79 | 11.85 | 467.56 |
| 5 | 9.50 | 16.97 | 332.35 |
| 6 | 9.06 | 21.03 | 389.06 |
| 7 | 4.19 | 16.61 | 203.61 |
| 8 | 2.54 | 17.65 | 302.84 |
| 9 | 3.63 | 5.14 | 120.38 |
| 10 | 3.98 | 18.09 | 209.41 |
| 11 | 7.74 | 31.96 | 410.40 |
| 12 | 8.45 | 13.99 | 235.50 |
| 13 | 17.97 | 14.62 | 507.18 |
| 14 | 7.79 | 9.02 | 152.76 |
| 15 | 11.63 | 11.49 | 133.46 |
| 16 | 10.80 | 27.96 | 227.84 |
| 17 | 6.41 | 33.78 | 531.19 |
| 18 | 3.26 | 21.79 | 133.11 |
| 19 | 1.19 | 19.78 | 515.70 |
| 20 | 3.12 | 22.45 | 202.82 |
| 21 | 10.36 | 15.72 | 361.06 |
| 22 | 9.35 | 15.58 | 523.08 |
| 23 | 8.26 | 16.98 | 397.43 |
| 24 | 5.00 | 28.54 | 238.80 |
| 25 | 5.70 | 35.84 | 277.39 |
| 26 | 7.72 | 26.67 | 194.24 |
| 27 | 7.52 | 33.63 | 402.37 |
| 28 | 6.36 | 18.63 | 305.12 |
| 29 | 5.19 | 21.92 | 258.19 |
| 30 | 5.29 | 27.45 | 330.53 |
| 31 | 7.15 | 24.92 | 305.62 |
| 32 | 24.99 | 4.77 | 406.70 |
| 33 | 50.32 | 29.06 | 463.94 |
| 34 | 27.76 | 9.57 | 503.95 |
| 35 | 5.92 | 26.11 | 281.84 |
| 36 | 6.36 | 21.80 | 146.90 |
| 37 | 4.89 | 13.05 | 233.95 |
| 38 | 7.63 | 20.76 | 208.99 |
| 39 | 19.90 | 19.42 | 283.73 |
| 40 | 9.00 | 27.90 | 422.11 |
| 41 | 7.65 | 12.63 | 491.09 |
| 42 | 11.72 | 20.10 | 321.69 |
| 43 | 7.80 | 19.76 | 408.24 |
| 44 | 7.32 | 54.98 | 393.12 |
| 45 | 6.41 | 26.76 | 262.23 |

TABLE 1-continued

Binding affinities to HEK293 EBNA cells expressing human (h) receptors of representative examples.

| Ex | $D_3 K_i$ (nM) | $5HT_{2A} K_i$ (nM) | $D_2 K_i$ (nM) |
|---|---|---|---|
| 46 | 47.56 | 14.39 | 463.70 |
| 47 | 7.61 | 24.05 | 165.40 |
| 48 | 13.82 | 9.52 | 183.74 |
| 49 | 6.09 | 8.17 | 245.32 |
| 50 | 40.94 | 19.04 | 245.54 |
| 51 | 13.85 | 25.01 | 351.61 |
| 52 | 16.28 | 4.57 | 130.00 |
| 53 | 8.81 | 29.63 | 351.77 |
| 54 | 8.00 | 16.92 | 100.30 |
| 55 | 4.63 | 27.00 | 164.90 |
| 56 | 10.11 | 18.51 | 593.34 |
| 57 | 6.16 | 23.07 | 370.18 |
| 58 | 3.70 | 20.15 | 345.34 |
| 59 | 4.02 | 36.74 | 324.88 |
| 60 | 6.73 | 21.75 | 1047.58 |
| 61 | 35.13 | 5.91 | 149.51 |
| 62 | 38.96 | 22.06 | 225.02 |
| 63 | 8.13 | 34.30 | 360.81 |
| 64 | 11.08 | 10.70 | 268.44 |
| 65 | 9.09 | 21.41 | 297.86 |
| 66 | 17.49 | 3.93 | 218.85 |
| 67 | 38.58 | 11.58 | 196.50 |
| 68 | 19.75 | 30.97 | 103.73 |
| 69 | 10.48 | 31.32 | 413.56 |
| 70 | 3.65 | 52.25 | 63.45 |
| 71 | 2.63 | 65.55 | 104.22 |
| 72 | 12.42 | 64.77 | 114.29 |
| 73 | 21.36 | 37.38 | 346.12 |
| 74 | 5.12 | 25.37 | 229.19 |
| 75 | 32.92 | 45.55 | 52.74 |
| 76 | 12.40 | 39.89 | 229.70 |
| 77 | 23.63 | 223.52 | 2707.02 |
| 78 | 11.59 | 20.67 | 229.21 |
| 79 | 6.11 | 56.15 | 229.43 |

The invention claimed is:

1. A compound of formula (I)

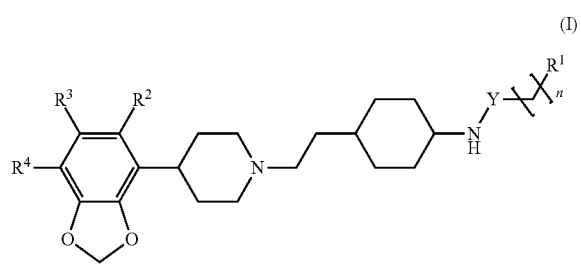

(I)

wherein n is 0, 1, 2 or 3;

Y is —C(O)— or —S(O)$_2$—;

$R^1$ is hydrogen, halogen, cyano, alkyl, haloalkyl, hydroxy, alkoxy, haloalkoxy, cycloalkyl, heterocycloalkyl, aryl, heteroaryl, —NR$^7$R$^8$, —C(O)—NR$^7$R$^8$, or —S(O)$_2$—R$^9$;

wherein alkyl, haloalkyl, and alkoxy are each optionally substituted by one, two or three independent R$^5$; and wherein cycloalkyl, heterocycloalkyl, aryl, and heteroaryl are each optionally substituted by one, two or three independent R$^6$;

$R^2$, $R^3$, and $R^4$ are each independently hydrogen, halogen, cyano, alkyl, haloalkyl, hydroxy, alkoxy or haloalkoxy;

$R^5$ is cyano, hydroxy, alkoxy, cycloalkyl, heterocycloalkyl, aryl, or heteroaryl, wherein cycloalkyl, heterocycloalkyl, aryl, and heteroaryl are each optionally substituted by one, two or three independent R$^6$;

$R^6$ is halogen, cyano, alkyl, haloalkyl, hydroxy, alkoxy, haloalkoxy, oxo, cycloalkyl, heterocycloalkyl, aryl, or heteroaryl;

$R^7$ and $R^8$ are each independently hydrogen, alkyl, cycloalkyl, cycloalkylalkyl, heterocycloalkyl, heterocycloalkylalkyl, aryl, or heteroaryl;

wherein cycloalkyl, heterocycloalkyl, aryl, and heteroaryl are each optionally substituted by one, two or three independent R$^{10}$;

$R^9$ is alkyl, cycloalkyl, heterocycloalkyl, aryl, heteroaryl, or —NR$^7$R$^8$;

wherein cycloalkyl, heterocycloalkyl, aryl, and heteroaryl are each optionally substituted by one, two or three independent R$^{11}$;

$R^{10}$ is halogen, cyano, alkyl, haloalkyl, hydroxy, alkoxy, haloalkoxy, or oxo; and $R^{11}$ is halogen, cyano, alkyl, haloalkyl, hydroxy, alkoxy, haloalkoxy, or oxo;

or a pharmaceutically acceptable salt or ester thereof.

2. The compound of claim 1, wherein n is 0, 1, 2 or 3;

Y is —C(O)— or —S(O)$_2$—;

$R^1$ is hydrogen, cyano, alkyl, haloalkyl, hydroxy, alkoxy, haloalkoxy, cycloalkyl, heterocycloalkyl, aryl, heteroaryl, —NR$^7$R$^8$, —C(O)—NR$^7$R$^8$, or —S(O)$_2$—R$^9$;

wherein alkyl, haloalkyl, and alkoxy are each optionally substituted by one, two or three independent R$^5$; and wherein cycloalkyl, heterocycloalkyl, aryl, and heteroaryl are each optionally substituted by one, two or three independent R$^6$;

$R^2$, $R^3$, and $R^4$ are each independently hydrogen, halogen, cyano, alkyl, haloalkyl, hydroxy, alkoxy or haloalkoxy;

$R^5$ is cyano, hydroxy, alkoxy, cycloalkyl, heterocycloalkyl, aryl, or heteroaryl, wherein cycloalkyl, heterocycloalkyl, aryl, and heteroaryl are each optionally substituted by one, two or three independent R$^6$;

$R^6$ is halogen, cyano, alkyl, haloalkyl, hydroxy, alkoxy, haloalkoxy, oxo, cycloalkyl, heterocycloalkyl, aryl, or heteroaryl;

$R^7$ and $R^8$ are each independently hydrogen, alkyl, cycloalkyl, cycloalkylalkyl, heterocycloalkyl, heterocycloalkylalkyl, aryl, or heteroaryl; and $R^9$ is alkyl, cycloalkyl, cycloalkylalkyl, heterocycloalkyl, heterocycloalkylalkyl, aryl, or heteroaryl;

or a pharmaceutically acceptable salt or ester thereof.

3. The compound of claim 1, wherein n is 0 or 1.

4. The compound of claim 1, wherein Y is —C(O)—.

5. The compound of claim 1, wherein $R^1$ is hydrogen, halogen, cyano, alkyl, haloalkyl, hydroxy, alkoxy, cycloalkyl, heterocycloalkyl, aryl, heteroaryl, —NR$^7$R$^8$, or —S(O)$_2$—R$^9$; wherein alkyl, haloalkyl, and alkoxy are each optionally substituted by one, two or three independent R$^5$; and wherein cycloalkyl, heterocycloalkyl, aryl, and heteroaryl are each optionally substituted by one, two or three independent R$^6$.

6. The compound of claim 1, wherein $R^1$ is alkyl, alkoxy, cycloalkyl, heterocycloalkyl, aryl, or heteroaryl; wherein alkyl, and alkoxy are each optionally substituted by one, two or three independent R$^5$; and wherein cycloalkyl, heterocycloalkyl, aryl, and heteroaryl are each optionally substituted by one, two or three independent R$^6$.

7. The compound of claim 1, wherein $R^1$ is methoxy-ethyl, isopropyl, hydroxy-isopropyl, hydroxy-isobutyl, methoxy, cyclopropyl, hydroxy-cyclopropyl, hydroxy-cyclohexyl, tetrahydropyranyl, dioxanyl, phenyl, or methyl-isoxazolyl.

8. The compound of claim 1, wherein $R^2$, $R^3$ and $R^4$ are hydrogen.

9. The compound of claim 1, wherein $R^5$ is hydroxy or alkoxy.

10. The compound of claim 1, wherein $R^6$ is halogen, cyano, alkyl, haloalkyl, hydroxy, alkoxy, oxo, or heterocycloalkyl.

11. The compound of claim 10, wherein $R^6$ is alkyl, hydroxy, or alkoxy.

12. The compound of claim 11, wherein $R^6$ is methyl, hydroxy, or methoxy.

13. The compound of claim 1, wherein $R^7$ and $R^8$ are each independently hydrogen, alkyl, or aryl; wherein aryl is optionally substituted by one halogen.

14. The compound of claim 1, wherein $R^9$ is alkyl, heterocycloalkyl, aryl, heteroaryl, or —$NR^7R^8$; wherein heterocycloalkyl, aryl, and heteroaryl are each optionally substituted by one halogen or alkyl.

15. The compound of claim 1, selected from the group consisting of:
Trans-N-{4-[2-(4-Benzo[1,3]dioxol-4-yl-piperidin-1-yl)-ethyl]-cyclohexyl}-acetamide;
Trans-N-{4-[2-(4-Benzo[1,3]dioxol-4-yl-piperidin-1-yl)-ethyl]-cyclohexyl}-3-methoxy-propionamide;
Trans-N-{4-[2-(4-Benzo[1,3]dioxol-4-yl-piperidin-1-yl)-ethyl]-cyclohexyl}-2-[1,4]dioxan-2-yl-acetamide;
Trans-N-{4-[2-(4-Benzo[1,3]dioxol-4-yl-piperidin-1-yl)-ethyl]-cyclohexyl}-2-(S)-[1,4]dioxan-2-yl-acetamide;
Trans-N-{4-[2-(4-Benzo[1,3]dioxol-4-yl-piperidin-1-yl)-ethyl]-cyclohexyl}-2-(R)-[1,4]dioxan-2-yl-acetamide;
Trans-N-{4-[2-(4-Benzo[1,3]dioxol-4-yl-piperidin-1-yl)-ethyl]-cyclohexyl}-2-(tetrahydro-furan-2-yl)-acetamide;
Trans-N-{4-[2-(4-Benzo[1,3]dioxol-4-yl-piperidin-1-yl)-ethyl]-cyclohexyl}-propionamide;
Trans-N-{4-[2-(4-Benzo[1,3]dioxol-4-yl-piperidin-1-yl)-ethyl]-cyclohexyl}-2-cyclopropyl-acetamide;
Trans-N-{4-[2-(4-Benzo[1,3]dioxol-4-yl-piperidin-1-yl)-ethyl]-cyclohexyl}-benzamide; and
Trans-N-{4-[2-(4-Benzo[1,3]dioxol-4-yl-piperidin-1-yl)-ethyl]-cyclohexyl}-3,3,3-trifluoro-propionamide;
or a pharmaceutically acceptable salt or ester thereof.

16. The compound of claim 1, selected from the group consisting of:
Trans-N-{4-[2-(4-Benzo[1,3]dioxol-4-yl-piperidin-1-yl)-ethyl]-cyclohexyl}-4,4,4-trifluoro-butyramide;
Trans-N-{4-[2-(4-Benzo[1,3]dioxol-4-yl-piperidin-1-yl)-ethyl]-cyclohexyl}-3,3,3-trifluoro-2-hydroxy-propionamide;
Trans-N-{4-[2-(4-Benzo[1,3]dioxol-4-yl-piperidin-1-yl)-ethyl]-cyclohexyl}-2-methoxy-acetamide;
Trans-N-{4-[2-(4-Benzo[1,3]dioxol-4-yl-piperidin-1-yl)-ethyl]-cyclohexyl}-4-cyano-benzamide;
Trans-N-{4-[2-(4-Benzo[1,3]dioxol-4-yl-piperidin-1-yl)-ethyl]-cyclohexyl}-6-methyl-nicotinamide;
Trans-N-{4-[2-(4-Benzo[1,3]dioxol-4-yl-piperidin-1-yl)-ethyl]-cyclohexyl}-2-(R)-tetrahydro-furan-2-yl-acetamide;
Trans-N-{4-[2-(4-Benzo[1,3]dioxol-4-yl-piperidin-1-yl)-ethyl]-cyclohexyl}-2-(S)-tetrahydro-furan-2-yl-acetamide;
Trans-{4-[2-(4-Benzo[1,3]dioxol-4-yl-piperidin-1-yl)-ethyl]-cyclohexyl}-carbamic acid methyl ester;
Trans-N-{4-[2-(4-Benzo[1,3]dioxol-4-yl-piperidin-1-yl)-ethyl]-cyclohexyl}-2-(3-methyl-isoxazol-5-yl)-acetamide; and
Trans-N-{4-[2-(4-Benzo[1,3]dioxol-4-yl-piperidin-1-yl)-ethyl]-cyclohexyl}-2-cyano-acetamide;
or a pharmaceutically acceptable salt or ester thereof.

17. The compound of claim 1, selected from the group consisting of:
Trans-N-{4-[2-(4-Benzo[1,3]dioxol-4-yl-piperidin-1-yl)-ethyl]-cyclohexyl}-2-(1-hydroxy-cyclohexyl)-acetamide;
Trans-N-{4-[2-(4-Benzo[1,3]dioxol-4-yl-piperidin-1-yl)-ethyl]-cyclohexyl}-2-(tetrahydro-pyran-2-yl)-acetamide;
Trans-N-{4-[2-(4-Benzo[1,3]dioxol-4-yl-piperidin-1-yl)-ethyl]-cyclohexyl}-isobutyramide;
Trans-N-{4-[2-(4-Benzo[1,3]dioxol-4-yl-piperidin-1-yl)-ethyl]-cyclohexyl}-3-methyl-butyramide;
Trans-N-{4-[2-(4-Benzo[1,3]dioxol-4-yl-piperidin-1-yl)-ethyl]-cyclohexyl}-butyramide;
Trans-2,2-Difluoro-cyclopropanecarboxylic acid {4-[2-(4-benzo[1,3]dioxol-4-yl-piperidin-1-yl)-ethyl]-cyclohexyl}-amide;
Trans-N-{4-[2-(4-Benzo[1,3]dioxol-4-yl-piperidin-1-yl)-ethyl]-cyclohexyl}-3-methoxy-butyramide;
3-Chloro-cyclobutanecarboxylic acid trans-{4-[2-(4-benzo[1,3]dioxol-4-yl-piperidin-1-yl)-ethyl]-cyclohexyl}-amide;
Trans-N-{4-[2-(4-Benzo[1,3]dioxol-4-yl-piperidin-1-yl)-ethyl]-cyclohexyl}-2-oxetan-3-yl-acetamide; and
Trans-N-{4-[2-(4-Benzo[1,3]dioxol-4-yl-piperidin-1-yl)-ethyl]-cyclohexyl}-2-(1R,3R)-3-methoxy-cyclopentyl)-acetamide;
or a pharmaceutically acceptable salt or ester thereof.

18. The compound of claim 1, selected from the group consisting of:
Trans-N-{4-[2-(4-Benzo[1,3]dioxol-4-yl-piperidin-1-yl)-ethyl]-cyclohexyl}-2-(4-hydroxy-tetrahydro-pyran-4-yl)-acetamide;
Trans-N-{4-[2-(4-Benzo[1,3]dioxol-4-yl-piperidin-1-yl)-ethyl]-cyclohexyl}-2-hydroxy-2-methyl-propionamide;
Trans-(S)—N-{4-[2-(4-Benzo[1,3]dioxol-4-yl-piperidin-1-yl)-ethyl]-cyclohexyl}-2-methoxy-propionamide;
Trans-(R)—N-{4-[2-(4-Benzo[1,3]dioxol-4-yl-piperidin-1-yl)-ethyl]-cyclohexyl}-2-methoxy-propionamide;
Trans-N-{4-[2-(4-Benzo[1,3]dioxol-4-yl-piperidin-1-yl)-ethyl]-cyclohexyl}-3-hydroxy-3-methyl-butyramide;
Trans-N-{4-[2-(4-Benzo[1,3]dioxol-4-yl-piperidin-1-yl)-ethyl]-cyclohexyl}-4-chloro-benzamide;
Trans-N-{4-[2-(4-Benzo[1,3]dioxol-4-yl-piperidin-1-yl)-ethyl]-cyclohexyl}-4-fluoro-benzamide;
Trans-(S)—N-{4-[2-(4-Benzo[1,3]dioxol-4-yl-piperidin-1-yl)-ethyl]-cyclohexyl}-3,3,3-trifluoro-2-hydroxy-propionamide;
Trans-(R)—N-{4-[2-(4-Benzo[1,3]dioxol-4-yl-piperidin-1-yl)-ethyl]-cyclohexyl}-3,3,3-trifluoro-2-hydroxy-propionamide; and
Trans-N-{4-[2-(4-Benzo[1,3]dioxol-4-yl-piperidin-1-yl)-ethyl]-cyclohexyl}-2-(S)-tetrahydro-pyran-2-yl-acetamide;
or a pharmaceutically acceptable salt or ester thereof.

19. The compound of claim 1, selected from the group consisting of:
Trans-N-{4-[2-(4-Benzo[1,3]dioxol-4-yl-piperidin-1-yl)-ethyl]-cyclohexyl}-2-(R)-tetrahydro-pyran-2-yl-acetamide;

Trans-N-{4-[2-(4-Benzo[1,3]dioxol-4-yl-piperidin-1-yl)-ethyl]-cyclohexyl}-2-(S)-tetrahydro-pyran-3-yl-acetamide;

Trans-N-{4-[2-(4-Benzo[1,3]dioxol-4-yl-piperidin-1-yl)-ethyl]-cyclohexyl}-2-(R)-tetrahydro-pyran-3-yl-acetamide;

Trans-N-{4-[2-(4-Benzo[1,3]dioxol-4-yl-piperidin-1-yl)-ethyl]-cyclohexyl}-3-ethoxy-propionamide;

Trans-N-{4-[2-(4-Benzo[1,3]dioxol-4-yl-piperidin-1-yl)-ethyl]-cyclohexyl}-2-(1-hydroxy-cyclobutyl)-acetamide;

Tetrahydro-furan-2-carboxylic acid-trans-{4-[2-(4-benzo[1,3]dioxol-4-yl-piperidin-1-yl)-ethyl]-cyclohexyl}-amide;

Tetrahydro-furan-3-carboxylic acid-trans-{4-[2-(4-benzo[1,3]dioxol-4-yl-piperidin-1-yl)-ethyl]-cyclohexyl}-amide;

Tetrahydro-pyran-4-carboxylic acid-trans-{4-[2-(4-benzo[1,3]dioxol-4-yl-piperidin-1-yl)-ethyl]-cyclohexyl}-amide;

1-Hydroxy-cyclopropanecarboxylic acid-trans-{4-[2-(4-benzo[1,3]dioxol-4-yl-piperidin-1-yl)-ethyl]-cyclohexyl}-amide; and Trifluoromethyl-cyclopropanecarboxylic acid-trans-{4-[2-(4-benzo[1,3]dioxol-4-yl-piperidin-1-yl)-ethyl]-cyclohexyl}-amide;

or a pharmaceutically acceptable salt or ester thereof.

20. The compound of claim 1, selected from the group consisting of:

Trans-N-{4-[2-(4-Benzo[1,3]dioxol-4-yl-piperidin-1-yl)-ethyl]-cyclohexyl}-2-methyl-butyramide;

1,1-Dioxo-tetrahydro-thiophene-3-carboxylic acid-trans-{4-[2-(4-benzo[1,3]dioxol-4-yl-piperidin-1-yl)-ethyl]-cyclohexyl}-amide;

Trans-N-{4-[2-(4-Benzo[1,3]dioxol-4-yl-piperidin-1-yl)-ethyl]-cyclohexyl}-2-(tetrahydro-pyran-4-yl)-acetamide;

Cyclobutanecarboxylic acid-trans-{4-[2-(4-benzo[1,3]dioxol-4-yl-piperidin-1-yl)-ethyl]-cyclohexyl}-amide;

Trans-N-{4-[2-(4-Benzo[1,3]dioxol-4-yl-piperidin-1-yl)-ethyl]-cyclohexyl}-2-methanesulfonyl-acetamide;

Trans-N-{4-[2-(4-Benzo[1,3]dioxol-4-yl-piperidin-1-yl)-ethyl]-cyclohexyl}-4-morpholin-4-yl-benzamide;

Quinoline-4-carboxylic acid-trans-N-{4-[2-(4-benzo[1,3]dioxol-4-yl-piperidin-1-yl)-ethyl]-cyclohexyl}-amide;

2,3-Dihydro-benzo[1,4]dioxine-6-carboxylic acid-trans-N-{4-[2-(4-benzo[1,3]dioxol-4-yl-piperidin-1-yl)-ethyl]-cyclohexyl}-amide;

2-Benzo[1,3]dioxol-5-yl-trans-N-{4-[2-(4-benzo[1,3]dioxol-4-yl-piperidin-1-yl)-ethyl]-cyclohexyl}-acetamide; and Chroman-3-carboxylic acid-trans-N-{4-[2-(4-benzo[1,3]dioxol-4-yl-piperidin-1-yl)-ethyl]-cyclohexyl}-amide;

or a pharmaceutically acceptable salt thereof.

21. The compound of claim 1, selected from the group consisting of:

1-Methyl-piperidine-4-carboxylic acid-trans-N-{4-[2-(4-benzo[1,3]dioxol-4-yl-piperidin-1-yl)-ethyl]-cyclohexyl}-amide;

3-Methyl-oxetane-3-carboxylic acid-trans-N-{4-[2-(4-benzo[1,3]dioxol-4-yl-piperidin-1-yl)-ethyl]-cyclohexyl}-amide;

Trans-N-{4-[2-(4-Benzo[1,3]dioxol-4-yl-piperidin-1-yl)-ethyl]-cyclohexyl}-2-(4-methoxy-cyclohexyl)-acetamide;

(R)-trans-N-{4-[2-(4-Benzo[1,3]dioxol-4-yl-piperidin-1-yl)-ethyl]-cyclohexyl}-2-hydroxy-propionamide;

Trans-N-{4-[2-(4-Benzo[1,3]dioxol-4-yl-piperidin-1-yl)-ethyl]-cyclohexyl}-2-hydroxy-acetamide;

1-Hydroxy-cyclohexanecarboxylic acid-trans-N-{4-[2-(4-benzo[1,3]dioxol-4-yl-piperidin-1-yl)-ethyl]-cyclohexyl}-amide;

1-Methoxy-cyclohexanecarboxylic acid-trans-N-{4-[2-(4-benzo[1,3]dioxol-4-yl-piperidin-1-yl)-ethyl]-cyclohexyl}-amide;

Trans-N-{4-[2-(4-Benzo[1,3]dioxol-4-yl-piperidin-1-yl)-ethyl]-cyclohexyl}-2-(4-methylpiperazin-1-yl)-acetamide;

Trans-N-{4-[2-(4-Benzo[1,3]dioxol-4-yl-piperidin-1-yl)-ethyl]-cyclohexyl}-methanesulfonamide; and Trans-N-{4-[2-(4-Benzo[1,3]dioxol-4-yl-piperidin-1-yl)-ethyl]-cyclohexyl}-benzenesulfonamide;

or a pharmaceutically acceptable salt or ester thereof.

22. The compound of claim 1, selected from the group consisting of:

N-trans-{4-[2-(4-Benzo[1,3]dioxol-4-yl-piperidin-1-yl)-ethyl]-cyclohexyl}-4-fluoro-benzenesulfonamide;

1-Methyl-1H-imidazole-4-sulfonic acid-trans-N-{4-[2-(4-benzo[1,3]dioxol-4-yl-piperidin-1-yl)-ethyl]-cyclohexyl}-amide;

Trans-N-{4-[2-(4-Benzo[1,3]dioxol-4-yl-piperidin-1-yl)-ethyl]-cyclohexyl}-2,2,2-trifluoro-acetamide;

2,3-Dihydro-indole-1-carboxylic acid N-trans-{4-[2-(4-benzo[1,3]dioxol-4-yl-piperidin-1-yl)-ethyl]-cyclohexyl}-amide;

N-Trans-3-{4-[2-(4-Benzo[1,3]dioxol-4-yl-piperidin-1-yl)-ethyl]-cyclohexyl}-1,1-dimethyl-urea;

Trans-N-{4-[2-(4-Benzo[1,3]dioxol-4-yl-piperidin-1-yl)-ethyl]-cyclohexyl}-2-fluoro-acetamide;

N-trans-1-{4-[2-(4-Benzo[1,3]dioxol-4-yl-piperidin-1-yl)-ethyl]-cyclohexyl}-3-(4-chloro-phenyl)-urea;

Trans-N-{4-[2-(4-benzo[1,3]dioxol-4-yl-piperidin-1-yl)-ethyl]-cyclohexyl}-N,N-dimethyl-sulfamide; and Morpholine-4-sulfonic acid-Trans-N-{4-[2-(4-benzo[1,3]dioxol-4-yl-piperidin-1-yl)-ethyl]-cyclohexyl}-amide;

or a pharmaceutically acceptable salt or ester thereof.

23. The compound of claim 1, selected from the group consisting of:

Trans-N-{4-[2-(4-Benzo[1,3]dioxol-4-yl-piperidin-1-yl)-ethyl]-cyclohexyl}-2-(S)-[1,4]dioxan-2-yl-acetamide;

Trans-N-{4-[2-(4-Benzo[1,3]dioxol-4-yl-piperidin-1-yl)-ethyl]-cyclohexyl}-2-(R)-[1,4]dioxan-2-yl-acetamide;

Trans-N-{4-[2-(4-Benzo[1,3]dioxol-4-yl-piperidin-1-yl)-ethyl]-cyclohexyl}-2-cyclopropyl-acetamide;

Trans-N-{4-[2-(4-Benzo[1,3]dioxol-4-yl-piperidin-1-yl)-ethyl]-cyclohexyl}-benzamide;

Trans-N-{4-[2-(4-Benzo[1,3]dioxol-4-yl-piperidin-1-yl)-ethyl]-cyclohexyl}-2-methoxy-acetamide;

Trans-N-{4-[2-(4-Benzo[1,3]dioxol-4-yl-piperidin-1-yl)-ethyl]-cyclohexyl}-2-(3-methyl-isoxazol-5-yl)-acetamide; and Trans-N-{4-[2-(4-Benzo[1,3]dioxol-4-yl-piperidin-1-yl)-ethyl]-cyclohexyl}-2-(1-hydroxy-cyclohexyl)-acetamide; or a pharmaceutically acceptable salt or ester thereof.

24. The compound of claim 1, selected from the group consisting of:

Trans-N-{4-[2-(4-Benzo[1,3]dioxol-4-yl-piperidin-1-yl)-ethyl]-cyclohexyl}-2-(tetrahydro-pyran-2-yl)-acetamide;

Trans-N-{4-[2-(4-Benzo[1,3]dioxol-4-yl-piperidin-1-yl)-ethyl]-cyclohexyl}-isobutyramide;

Trans-N-{4-[2-(4-Benzo[1,3]dioxol-4-yl-piperidin-1-yl)-ethyl]-cyclohexyl}-2-hydroxy-2-methyl-propionamide;

Trans-(R)—N-{4-[2-(4-Benzo[1,3]dioxol-4-yl-piperidin-1-yl)-ethyl]-cyclohexyl}-2-methoxy-propionamide;

Trans-N-{4-[2-(4-Benzo[1,3]dioxol-4-yl-piperidin-1-yl)-ethyl]-cyclohexyl}-3-hydroxy-3-methyl-butyramide;

Trans-N-{4-[2-(4-Benzo[1,3]dioxol-4-yl-piperidin-1-yl)-ethyl]-cyclohexyl}-2-(R)-tetrahydro-pyran-2-yl-acetamide;

Trans-N-{4-[2-(4-Benzo[1,3]dioxol-4-yl-piperidin-1-yl)-ethyl]-cyclohexyl}-2-(R)-tetrahydro-pyran-3-yl-acetamide;

1-Hydroxy-cyclopropanecarboxylic acid-trans-{4-[2-(4-benzo[1,3]dioxol-4-yl-piperidin-1-yl)-ethyl]-cyclohexyl}-amide; and or a pharmaceutically acceptable salt and ester thereof.

25. A pharmaceutical composition comprising a therapeutically effective amount of a compound of formula I

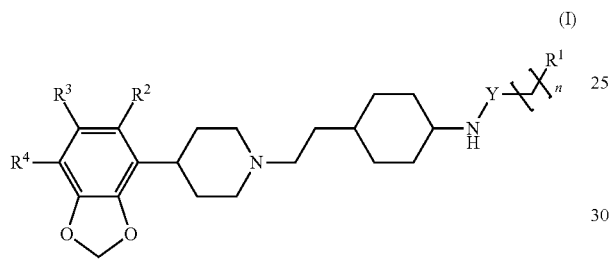

(I)

wherein
n is 0, 1, 2 or 3;
Y is —C(O)— or —S(O)$_2$—;

$R^1$ is hydrogen, halogen, cyano, alkyl, haloalkyl, hydroxy, alkoxy, haloalkoxy, cycloalkyl, heterocycloalkyl, aryl, heteroaryl, —NR$^7$R$^8$, —C(O)—NR$^7$R$^8$, or —S(O)$_2$—R$^9$;

wherein alkyl, haloalkyl, and alkoxy are each optionally substituted by one, two or three independent R$^5$; and wherein cycloalkyl, heterocycloalkyl, aryl, and heteroaryl are each optionally substituted by one, two or three independent R$^6$;

$R^2$, $R^3$, and $R^4$ are each independently hydrogen, halogen, cyano, alkyl, haloalkyl, hydroxy, alkoxy or haloalkoxy;

$R^5$ is cyano, hydroxy, alkoxy, cycloalkyl, heterocycloalkyl, aryl, or heteroaryl, wherein cycloalkyl, heterocycloalkyl, aryl, and heteroaryl are each optionally substituted by one, two or three independent R$^6$;

$R^6$ is halogen, cyano, alkyl, haloalkyl, hydroxy, alkoxy, haloalkoxy, oxo, cycloalkyl, heterocycloalkyl, aryl, or heteroaryl;

$R^7$ and $R^8$ are each independently hydrogen, alkyl, cycloalkyl, cycloalkylalkyl, heterocycloalkyl, heterocycloalkylalkyl, aryl, or heteroaryl;

wherein cycloalkyl, heterocycloalkyl, aryl, and heteroaryl are each optionally substituted by one, two or three independent R$^{19}$;

$R^9$ is alkyl, cycloalkyl, heterocycloalkyl, aryl, heteroaryl, or —NR$^7$R$^8$;

wherein cycloalkyl, heterocycloalkyl, aryl, and heteroaryl are each optionally substituted by one, two or three independent R$^{11}$;

$R^{10}$ is halogen, cyano, alkyl, haloalkyl, hydroxy, alkoxy, haloalkoxy, or oxo; and $R^{11}$ is halogen, cyano, alkyl, haloalkyl, hydroxy, alkoxy, haloalkoxy, or oxo;

or a pharmaceutically acceptable salt or ester thereof
and a pharmaceutically acceptable carrier.

* * * * *